US010814612B2

(12) United States Patent
Rossignol

(10) Patent No.: US 10,814,612 B2
(45) Date of Patent: Oct. 27, 2020

(54) USE OF THIAZOLIDE COMPOUNDS FOR THE PREVENTION AND TREATMENT OF VIRAL DISEASES, CANCER AND DISEASES CAUSED BY INTRACELLULAR INFECTIONS

(71) Applicant: Romark Laboratories L.C., Tampa, FL (US)

(72) Inventor: Jean-Francois Rossignol, St. Petersburg, FL (US)

(73) Assignee: Romark Laboratories L.C., Tampa, FL (US)

(*) Notice: Subject to any disclaimer, the term of this patent is extended or adjusted under 35 U.S.C. 154(b) by 0 days.

(21) Appl. No.: 16/438,783

(22) Filed: Jun. 12, 2019

(65) Prior Publication Data
US 2019/0291404 A1 Sep. 26, 2019

Related U.S. Application Data

(63) Continuation of application No. 15/861,234, filed on Jan. 3, 2018, now Pat. No. 10,336,058, which is a continuation of application No. 13/471,948, filed on May 15, 2012, now abandoned.

(60) Provisional application No. 61/486,728, filed on May 16, 2011.

(51) Int. Cl.
A61K 31/42 (2006.01)
B41F 11/00 (2006.01)
A61K 39/39 (2006.01)
A61K 45/06 (2006.01)
A61K 31/426 (2006.01)
A61K 38/21 (2006.01)
A61K 38/47 (2006.01)
B41F 7/02 (2006.01)
B41F 7/06 (2006.01)
B41F 7/08 (2006.01)
B41F 9/02 (2006.01)
B41F 13/18 (2006.01)
B41F 13/193 (2006.01)
A61K 39/00 (2006.01)

(52) U.S. Cl.
CPC ............ *B41F 11/00* (2013.01); *A61K 31/426* (2013.01); *A61K 38/212* (2013.01); *A61K 38/47* (2013.01); *A61K 39/39* (2013.01); *A61K 45/06* (2013.01); *B41F 7/025* (2013.01); *B41F 7/06* (2013.01); *B41F 7/08* (2013.01); *B41F 9/021* (2013.01); *B41F 13/18* (2013.01); *B41F 13/193* (2013.01); *A61K 2039/55511* (2013.01); *Y02A 50/41* (2018.01); *Y02A 50/414* (2018.01); *Y02A 50/489* (2018.01)

(58) Field of Classification Search
CPC .................................................. A61K 31/426
See application file for complete search history.

(56) References Cited

U.S. PATENT DOCUMENTS

| | | |
|---|---|---|
| 5,859,038 A | 1/1999 | Rossignol |
| 5,886,013 A | 3/1999 | Rossignol |
| 5,935,591 A | 8/1999 | Rossignol et al. |
| 5,965,590 A | 10/1999 | Rossignol |
| 5,968,961 A | 10/1999 | Rossignol |
| 6,020,353 A | 2/2000 | Rossignol |
| 6,117,894 A | 9/2000 | Rossignol |
| 7,285,567 B2 | 10/2007 | Rossignol |
| 7,550,493 B2 | 6/2009 | Rossignol |
| 7,645,783 B2 | 1/2010 | Rossignol |
| 8,633,230 B2 | 1/2014 | Rossignol |
| 2006/0024365 A1 | 2/2006 | Vaya et al. |
| 2007/0015803 A1 | 1/2007 | Rossignol |
| 2007/0167504 A1 | 7/2007 | Rossignol |
| 2010/0081713 A1 | 4/2010 | Sharma et al. |
| 2010/0203056 A1 | 8/2010 | Irving et al. |
| 2010/0260797 A1 | 10/2010 | Hanon |
| 2010/0330173 A1 | 12/2010 | Rossignol et al. |
| 2011/0020272 A1 | 1/2011 | Schubert |
| 2011/0098248 A1 | 4/2011 | Halcomb et al. |

FOREIGN PATENT DOCUMENTS

| | | |
|---|---|---|
| JP | 2008-538362 A | 10/2008 |
| WO | WO 2006/110814 A2 | 10/2006 |
| WO | WO 2010/151577 A1 | 12/2010 |
| WO | WO 2011/106445 A1 | 9/2011 |
| WO | WO 2012/139028 A2 | 10/2012 |

OTHER PUBLICATIONS

HIV Vaccines [online]. Retrieved from the internet on Jul. 6, 2017 URL: <http://www.hiv.gov/hiv-basics/hiv-prevention/potential-future-options/hiv-vaccines>.*
HIV Vaccine: How Close Are We? [online]. Retrieved from the internet on Jul. 6, 2017 URL: <http://www.healthline.com/health/hiv-aids/vaccine-how-close-are-we>.*
Cancer [online], retrieved on Jul. 6, 2007, from the internet, URL http://www.nlm.nih.gov/medlineplus/cancer.html, 10 pages.
Clerici et al., "The anti-infective Nitazoxanide shows strong immumodulating effects," The Journal of Immunology, 2011, 186:1550121, Abstract 155.21, one page.
Concise Encyclopedia Chemistry, 1993, Walter de Gruyter, Berlin, New York, 872-873.
Doumbo et al., "Nitazoxanide in the treatment of cryptosporidial diarrhea and other intestinal parasitic infections associated with acquired immunodeficiency syndrome in tropical Africa," Am. J. Trop. Med. Hyg., 1997, 56(6):637-639.
Fox, Nature Biotechnology, 2007, 25(12):1395-1402.
Gargala et al., "Evaluation of New Thiazolide/Thiadiazolide Derivatives Reveals Nitro Group-Independent Efficacy against In Vitro Development of *Cryptosporidium parvum*," Antimicrobial Agents and Chemotherapy, Mar. 2010, 54(3):1315-1318.
Golub et al., "Molecular Classification of Cancer: Class Discovery and Class Prediction by Gene Expression Monitoring," Science, 1999, 286:531-536.

(Continued)

*Primary Examiner* — Shawquia Jackson
(74) *Attorney, Agent, or Firm* — Foley & Lardner LLP

(57) ABSTRACT

The invention provides for the use of pharmaceutical compositions comprising a thiazolide in the stimulation of the immune system in a subject in need thereof, thereby preventing and/or treating viral diseases, cancer and diseases caused by intracellular protozoan infections.

14 Claims, 27 Drawing Sheets

(56) References Cited

OTHER PUBLICATIONS

Korba et al., "Nitazoxanide, tizoxanide and other thiazolides are potent inhibitors of hepatitis B virus and hepatitis C virus replication," Antiviral Research, 2008, 77:56-63.
Lala et al., "Role of nitric oxide in tumor progression: Lessons from experimental tumors," Cancer and Metastasis Reviews, 1998, 17(1):91-106.
Muller et al., "Thiazolides inhibit growth and induce glutathione-S-transferase Pi (GSTP1)-dependent cell death in human colon cancer cells," International Journal of Cancer, 2008, 123(8):1797-1806.
Tan et al., "Systems biology and the host response to viral infection," Nature, 2007, 25(12):1383-1389.
Meylan et al,. "Mechanisms for the Inhibition of HIV Replication by Interferons-$\alpha$, -$\beta$, and -$\gamma$ in Primary Human Macrophages," Virology, 1993, 193(1):138-148.
Sabbatini et al., "Qualitative Immune Modulation by Interleukin-2 (IL-2) Adjuvant Therapy in Immunological Non Responder HIV-Infected Patients," PlosOne, 2010, 5(11):e14119.

* cited by examiner

USE OF THIAZOLIDE COMPOUNDS FOR THE PREVENTION AND TREATMENT OF VIRAL DISEASES, CANCER AND DISEASES CAUSED BY INTRACELLULAR INFECTIONS

CROSS-REFERENCE TO RELATED PATENT APPLICATIONS

This application is a Continuation of U.S. application Ser. No. 15/861,234, filed Jan. 3, 2018, which is a Continuation of U.S. application Ser. No. 13/471,948, filed May 15, 2012, which claims priority from U.S. Provisional Application 61/486,728, filed May 16, 2011, incorporated herein by reference in its entirety.

FIELD OF THE INVENTION

The present invention is directed to compositions and methods for immunomodulation, including preventing or treating viral diseases, cancer and diseases caused by intracellular protozoan infections.

BACKGROUND OF THE INVENTION

Influenza is a highly contagious acute respiratory illness that affects all age groups and causes about 36,000 deaths and over 226,000 hospitalizations per year in the United States alone. Classified (as types A, B, and C), according to antigenic differences in their nucleoprotein and matrix protein, the influenza viruses are enveloped, negative-stranded RNA viruses. The many subtypes of influenza A virus differ in their two surface glycoproteins, hemagglutinin ("HA") and neuraminidase ("NA"), which are the main targets of the protective immune response, and are labeled according to the type of hemagglutinin (denoted with an H number) and neuraminidase (denoted with an N number). HA and NA vary continuously as a result of antigenic drift and antigenic shift. Sixteen H subtypes (or "serotypes") and nine N subtypes are known.

Hepatitis B is an infectious illness caused by hepatitis B virus (HBV). About a quarter of the world's population, more than 2 billion people, have been infected with the hepatitis B virus. The acute illness causes liver inflammation, vomiting, jaundice and rarely, death. Chronic hepatitis B may eventually cause liver cirrhosis and liver cancer-a fatal disease with very poor response to current chemotherapy. The hepatitis B virus has a circular genome composed of partially double-stranded DNA and, similar to retroviruses, replicates through an RNA intermediate by reverse transcription. Although replication takes place in the liver, the virus spreads to the blood where virus-specific proteins and their corresponding antibodies are found in infected people.

Cancer is characterized by the uncontrolled growth and spread of abnormal cells. Because tumor cells are derived from normal cells, the host immune system does not recognize tumor cell antigens as foreign. Further, some tumor cells have developed ways to escape the host immune defense system, by eliminating antigens or reducing the number of receptors on the surface of the cell.

Melanoma is a malignant skin cancer that originates in melanocytes. If detected and treated early, it is nearly 100 percent curable. Without early treatment the cancer can advance, spread and be fatal. Melanoma is the skin cancer that causes the most deaths. Superficial spreading melanoma is the most common type of melanoma, especially among young people. This melanoma affects the top layer of the skin for a fairly long time before penetrating more deeply. Lentigo maligna is found most often in the elderly who are chronically exposed to the sun. Acral lentiginous melanoma also spreads superficially before penetrating more deeply and is the most common melanoma in African-Americans and Asians, and the least common among Caucasians. Nodular melanoma is usually invasive at the time it is first diagnosed and is the most aggressive form of melanoma.

Leukemia is a blood or bone marrow cancer characterized by an abnormal increase of white blood cells. Hairy cell leukemia is an uncommon hematological malignancy characterized by an accumulation of abnormal B lymphocytes in the bone marrow, which interfere with the production of normal white blood cells, red blood cells and platelets. Chronic myeloid leukemia (CIVIL) is a cancer of the white blood cells characterized by the increased and unregulated growth of predominantly myeloid cells in the bone marrow and the accumulation of these cells in the blood. Non-Hodgkin lymphomas can be aggressive or indolent, may occur at any age and are often marked by lymph nodes that are larger than normal, fever, and weight loss. B cell non-Hodgkin lymphomas include Burkitt lymphoma, chronic lymphocytic leukemia/small lymphocytic lymphoma (CLL/SLL), diffuse large B-cell lymphoma, follicular lymphoma, immunoblastic large cell lymphoma, precursor B-lymphoblastic lymphoma and mantle cell lymphoma. T cell non-Hodgkin lymphomas include mycosis fungoides, anaplastic large cell lymphoma, and precursor T-lymphoblastic lymphoma.

Renal cell carcinoma, which includes renal cell carcinoma, renal pelvis carcinoma and Wilms tumor, is the most common type of kidney cancer in adults. In 2010, there were 58,240 estimated new cases and 13,040 deaths in the United States alone.

Although significant advances through molecular biology in the identification of tumor antigens and their production in recombinant and synthetic form have allowed many sophisticated approaches in cancer treatment, the immunogenic success of tumor cell vaccines ultimately depends on major histocompatibility complex (MHC) expression on antigen-presenting cells and the recognition of tumor antigens as "foreign" by the host immune system. Prevention and treatment, however, are hampered by the ability of pathogens to escape the host immune response.

Accordingly, there is a strong need in the art for the development of new prophylactic and treatment options for viral and cancer diseases.

Nitazoxanide (2-(acetylyloxy)-N-(5-nitro-2-thiazolyl) benzamide) is a thiazolide antiparasitic agent having the following structure:

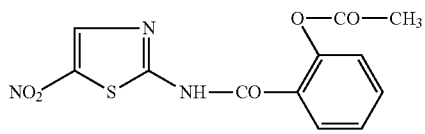 [SMILES: CC(=O)Oc1ccccc1C(=O)Nc1ncc([N+](=O)[O-])s1]

Tizoxanide is the active circulating metabolite of nitazoxanide. Following oral administration of nitazoxanide or mixtures of nitazoxanide plus tizoxanide in humans, these compounds are partially absorbed from the intestinal tract, and nitazoxanide is rapidly hydrolyzed to form tizoxanide in plasma. Tizoxanide is bound to plasma proteins and its urinary elimination half-life is 7.3 hours. Tizoxanide is glucurono-conjugated, and the drug is eliminated in urine and bile as tizoxanide or tizoxanide glucuronide. The half-life of tizoxanide in plasma is only approximately 1.5 hours. Tizoxanide has the following structure:

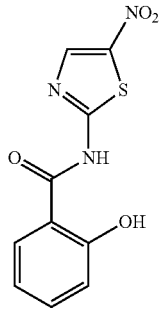 [SMILES: O=C(Nc1ncc([N+](=O)[O-])s1)c1ccccc1O]

RM-4848 is a substituted thiazolide having the same structure as tizoxanide, but including a chloro group substituted for the nitro group, thus resulting in the compound N-(5-chlorothiazol-2-yl)-2-hydroxybenzamide. Nitazoxanide (Alinia®, NTZ) and tizoxanide (TIZ) are thiazolide compounds with activity against parasites, anaerobic bacteria, and viruses. NTZ is approved in the United States for the treatment of diarrhea caused by *Cryptosporidium parvum* and *Giardia lamblia*. NTZ and TIZ also inhibit replication of RNA and DNA viruses including influenza A and hepatitis C viruses. In clinical trials, NTZ was shown to be effective in treating rotavirus gastroenteritis, norovirus gastroenteritis and chronic hepatitis C, and is in late-stage clinical development for treatment of influenza.

SUMMARY OF THE INVENTION

The invention provides for the use of pharmaceutical compositions comprising a thiazolide for immunomodulating a subject in need thereof, including for the prevention and/or treatment of viral diseases, cancer and diseases caused by intracellular protozoan or bacterial infections. In a specific embodiment, the invention provides a method of stimulating an immune response in a subject in need thereof, comprising administering to the subject a pharmaceutical composition comprising a therapeutically effective amount of a thiazolide compound. Acceptable thiazolide compounds of the invention include those disclosed in U.S. Pat. Nos. 7,645,783, 7,550,493, 7,285,567, 6,117,894, 6,020,353, 5,968,961, 5,965,590, 5,935,591, and 5,886,013, which are herein incorporated by reference in their entirety. In a preferred embodiment the thiazolide agent is nitazoxanide. In another preferred embodiment, the thiazolide agent is tizoxanide. In yet another preferred embodiment, the thiazolide agent is RM-4848 or its ester prodrug, RM-5038. In a preferred aspect of the invention, the subject suffers from a viral infection. In another preferred aspect of the invention, the subject is at risk of developing a viral infection. In one aspect of the invention, the viral infection is influenza. The influenza may be caused by a virus selected from H1N1, H2N2, H3N2, H5N1, H7N7, H1N2, H9N2, H7N2, H7N3, and H10N7. In another aspect of the invention, the viral infection is Hepatitis B. In a preferred embodiment, the thiazolide compound is administered alone. In other preferred embodiments, the thiazolide compound is administered in combination with a neuraminidase inhibitor, such as Laninamivir, Oseltamivir, Zanamivir or Peramivir, or an immunostimulant, such as Imiquimod or Resiquimod, or an adamantine analogue, or a recombinant sialidase fusion protein, or an anti-hepatitis B drug. In yet another preferred embodiment, the thiazolide compound is administered in combination with a vaccine.

In another preferred aspect of the invention, the subject suffers from a cancer. In a different preferred aspect of the invention, the subject is at risk of developing a cancer. In one embodiment, the cancer is leukemia. Preferably, the leukemia is hairy cell leukemia or chronic myeloid leukemia. In a different aspect of the invention, the cancer is melanoma. In yet another aspect of the invention, the cancer is non-Hodgkin lymphoma. In a further aspect of the invention, the cancer is renal cell carcinoma. In one preferred embodiment, the thiazolide compound is administered alone. In another preferred embodiment of the invention, the thiazolide compound is administered in combination with a vaccine, or an immunostimulant, or an anticancer drug. The anticancer drug may include, but is not limited to, STI571, CGP 74588, 1-β-D-Arabinofuranosylcytosine (Ara-C), doxorbicin, dacarbazine, cisplatin, bleomycin, vincristine, lomustine, vinblastine, carmustine, DTIC, tamoxifen, sunitinib, sorafenib and interferon-α.

In another preferred aspect of the invention, the subject suffers from an intracellular protozoan infection. In a different preferred aspect of the invention, the subject is at risk of developing an intracellular protozoan infection. In one embodiment, the intracellular protozoan infection is *Cryptosporidium* spp. In a different aspect of the invention, the intracellular protozoan infection is *Leishmania* spp. In yet another aspect of the invention, the intracellular protozoan infection is *Toxoplasma gondii*. In a further aspect of the invention, the intracellular protozoan infection is *Trypanosoma cruzii*. In one preferred embodiment, the thiazolide compound is administered alone.

In another preferred embodiment of the invention, the thiazolide compound is administered in combination with a vaccine, or an immunostimulant, or an antiprotozoal drug. The antiprotozoal drug may include, but is not limited to, trimethoprim/sulfamethoxazole, atovaquone, clindamycin, pyrimethamine, spiramycin, diminazine, homidium, suramin, melarsamine, sodium stibogluconate and meglumine antimoniate.

In another preferred aspect of the invention, the subject suffers from an intracellular bacterial infection. In a different preferred aspect of the invention, the subject is at risk of developing an intracellular bacterial infection. In one embodiment, the intracellular bacterial infection is *Mycobacterium tuberculosis*.

In one specific embodiment, the invention provides a method of treating or preventing a viral infection in a subject in need thereof comprising administering to the subject a pharmaceutical composition comprising a therapeutically effective amount of a thiazolide compound. In a preferred embodiment the thiazolide agent is nitazoxanide. In another preferred embodiment, the thiazolide agent is tizoxanide. In yet another preferred embodiment, the thiazolide agent is RM-4848 or a pharmaceutically acceptable prodrug thereof. In one aspect of the invention, the viral infection is influenza. The influenza may be caused from H1N1, H2N2, H3N2, H5N1, H7N7, H1N2, H9N2, H7N2, H7N3, and H10N7. In another aspect of the invention, the viral infection is Hepatitis B. In another aspect of the invention, the viral infection is diarrhea or gastroenteritis caused by rotavirus or norovirus. In a preferred embodiment, the thiazolide compound is administered alone. In other preferred embodiments, the thiazolide compound is administered in combination with a neuraminidase inhibitor, such as Laninamivir, Oseltamivir, Zanamivir or Peramivir, or an immunostimulant, such as Imiquimod or Resiquimod, or an adamantine analogue, or a recombinant sialidase fusion protein, or an anti-hepatitis B drug. In yet another preferred embodiment, the thiazolide compound is administered in combination with a vaccine.

In another specific embodiment, the invention provides a method of treating or preventing cancer in a subject in need thereof, comprising administering to the subject a pharmaceutical composition comprising a therapeutically effective amount of a thiazolide compound. In a preferred embodiment the thiazolide agent is nitazoxanide. In another preferred embodiment, the thiazolide agent is tizoxanide. In yet another preferred embodiment, the thiazolide agent is RM-4848. In a particular aspect of the invention, the cancer is leukemia. Preferably, the leukemia is hairy cell leukemia or chronic myeloid leukemia. In a different aspect of the invention, the cancer is melanoma. In yet another aspect of the invention, the cancer is non-Hodgkin lymphoma. In a further aspect of the invention, the cancer is renal cell carcinoma. In one preferred embodiment, the thiazolide compound is administered alone. In another preferred embodiment of the invention, the thiazolide compound is administered in combination with a vaccine, or an immunostimulant, or an anticancer drug. The anticancer drug may include, but is not limited to, STI571, CGP 74588, 1-β-D-Arabinofuranosylcytosine (Ara-C), doxorbicin, dacarbazine, cisplatin, bleomycin, vincristine, lomustine, vinblastine, carmustine, DTIC, tamoxifen, sunitinib, sorafenib and interferon-α.

In still another specific embodiment, the invention provides a method of treating or preventing intracellular protozoan infections in a subject in need thereof, comprising administering to the subject a pharmaceutical composition comprising a therapeutically effective amount of a thiazolide compound. In a preferred embodiment the thiazolide agent is nitazoxanide. In another preferred embodiment, the thiazolide agent is tizoxanide. In yet another preferred embodiment, the thiazolide agent is RM-4848. In a particular aspect of the invention, the intracellular protozoan infection is *Cryptosporidium* spp. In a different aspect of the invention, the cancer is melanoma. In a different aspect of the invention, the intracellular protozoan infection is *Leishmania* spp. In yet another aspect of the invention, the intracellular protozoan infection is *Toxoplasma gondii*. In a further aspect of the invention, the intracellular protozoan infection is *Trypanosoma cruzii* In one preferred embodiment, the thiazolide compound is administered alone. In another preferred embodiment of the invention, the thiazolide compound is administered in combination with a vaccine, or an immunostimulant, or an antiprotozoal drug. The antiprotozoal drug may include, but is not limited to, trimethoprim/sulfamethoxazole, atovaquone, clindamycin, pyrimethamine, spiramycin, diminazine, homidium, suramin, melarsamine, sodium stibogluconate and meglumine antimoniate.

In subjects with immune deficiencies, the immune response required to effectively treat or prevent a viral disease, cancer or intracellular protozoan or bacterial infection may not be produced by thiazolides using the dosing regimen that is typically used to successfully treat a subject with a fully competent immune system. Subjects with extreme immune deficiencies may not be good candidates for treatment with thiazolides. Subjects with moderate immune deficiencies may require higher doses of thiazolide treatment, more frequent dosing, or dosing for a longer period of time than subjects with fully competent immune systems. Subjects with HIV infection who have not developed immune deficiencies may be effectively treated with thiazolides, while subjects with immune deficiencies associated with HIV infection may require treatment with antiretroviral drugs to reduce HIV viral titer and partially restore immune function before or simultaneously with thiazolide therapy. Thus, the use of thiazolides to stimulate immune response may be tailored for patients based on immune status.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE PREFERRED EMBODIMENTS

Figure 1A:
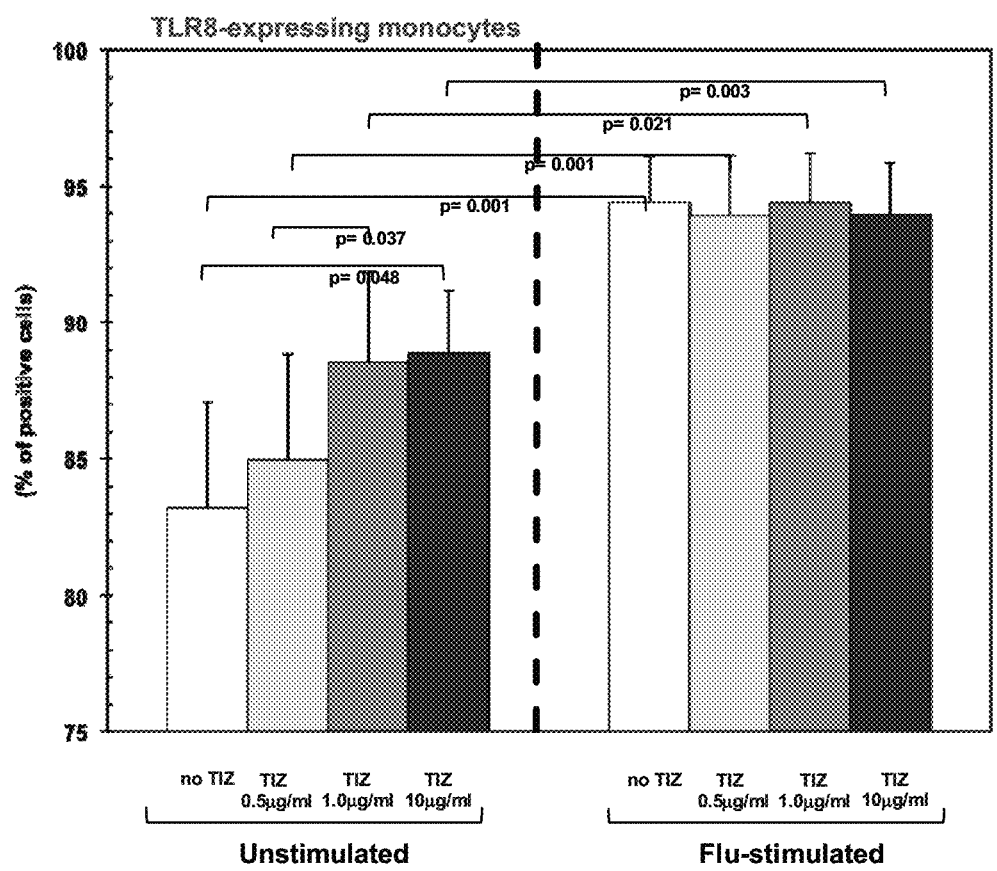
FIGS. 1A, 1B, and 1C are graphs expressing CD14+ monocytes in the absence or presence of different doses of Tizoxanide in unstimulated and Flu-stimulated conditions. Mean values, S.E. and p values are indicated.

Unless otherwise specified, "a" or "an" means "one or more."

The compositions and methods of the present invention are for stimulating an immune response in a subject in need thereof, thereby preventing and treating infections and/or cancer conditions. The aim of the invention is to provide effective, non-invasive methods to prevent and treat a viral infection, a cancer condition and/or diseases caused by intracellular protozoan infections in a subject in need thereof, by stimulating a strong immune response in the subject, which is mediated by both the innate and the acquired immune systems.

The innate immune system, which confers immediate, short-term defense against infection, provides for the recruitment of phagocytes and especially neutrophils at the site of inflammation, which in turn stimulate the release of leukocytes and lymphocytes, with the concomitant production of cytokines, including TNF, HMGB1 and IL-1. Innate leukocytes include natural killer cells, mast cells, eosinophils, basophils and phagocytes, including macrophages, neutrophils and dendritic cells. Toll-like receptors (TLRs) are key components of the innate immune system, as they detect microbial infection and trigger anti-microbial host defense responses. TLRs control multiple dendritic cell functions and trigger the cascade that leads to the acquired immune system response, including the production of type I interferons (I IFNs). TLRs 3, 7, 8 and 9 are involved in viral detection and recognize pathogen nucleic acids. TLRs 7, 8 and 9 are located in intracellular endolysosomal compartments.

The acquired or adaptive immune system, which is triggered in vertebrates when a pathogen evades the innate immune system, is responsible for the recognition of specific "non-self" antigens during antigen presentation and for the immune response aimed at eliminating foreign pathogens or pathogen infected cells. In the acquired immune system, the B cells are involved in the humoral immune response, and the T cells are responsible for cell-mediated immune responses. Antigen presentation by the dendritic cells stimulates T cells to become either "cytotoxic" CD8+ cells or "helper" CD4+ cells.

In the lymph nodes, the dendritic cells present the "non-self" antigens on their surface by coupling them to the Major histocompatibility complex (MHC, also known in humans as Human leukocyte antigen (HLA)), which is recognized by the T cells passing through the lymph nodes. Exogenous antigens are usually displayed on MHC class II molecules, which activate CD4+ helper T-cells. Endogenous antigens produced by viruses which replicate within a host cell, are typically displayed on MHC class I molecules, and activate CD8+ cytotoxic T-cells. The acquired immune system includes cytotoxic T cells, also known as TC, killer T cell, or cytotoxic T-lymphocyte (CTL). Once the T cell receptor (TCR) in the cytotoxic T cells interacts with a peptide-bound MHC class I molecule, the CTL become activated and turn into effector CTL, releasing cytotoxins, such as perforin and granulysin, which form pores in the target cell's plasma membrane. CTL activation is regulated by CD4+ lymphocytes or helper T cells. Helper T cells express T cell receptors (TCR) that recognize antigen bound to Class II MHC molecules. Effector CD4+ T helper cells may respond to an infection by triggering a Th1 or Th2 type response. The Th1 response leads to cell-mediated immunity and is characterized by the production of Interferon-gamma, which activates macrophages and induces B cells to produce antibodies. The Th2 response leads to humoral immunity and is characterized by the release of Interleukin 4, with the consequent activation of B cells and production of neutralizing antibodies. Generally, Th1 responses are more effective against intracellular pathogens, such as viruses and bacteria that are inside host cells, while Th2 responses are more effective against extracellular bacteria, parasites and toxins.

The present inventors discovered that the anti-viral effects of thiazolide agents, in particular nitazoxanide, tizoxanide and RM-4848, or a prodrug thereof, result from the immunomodulatory activity of these agents, which are capable of stimulating a strong immune response by activating both the innate and the acquired immune systems. In particular, the inventors of the present application discovered that nitazoxanide, tizoxanide and RM-4848 stimulate T helper cell and CTL activity, TLR7 and TLR8 expression and type I interferon response, by inducing an increase in: 1) IFNγ- and IL2-secreting CD4+ T cells, 2) CTL degranulation, 3) Fas-expressing CD8+ T cells, 4) TLR8-expressing monocytes, 5) IFNα- and IFNβ-mRNA expression, 6) mRNA specific for type I IFN inducible genes (MXA, PRKCZ, ADAR, CXCL10, IRF1, PRKRA), and 7) mRNA specific for gene involved in MHC class I presentation (HLA-A, HLA-B, TAP1). Accordingly, these thiazolide agents may be used for stimulating an immune response in a subject in need thereof, and in particular in subjects who are at risk of developing or are suffering from a disease where a strong immune response is needed, such as viral infection, a cancer or a disease caused by intracellular protozoan infection(s). Additionally, the methods of the invention can be used to alleviate the symptoms of the disease, or as a preventative measure in a subject.

The terms "subject" and "patient" are used interchangeably, and are meant to refer to any mammal, including humans, that has, or is at risk of developing, a viral infection or a cancer condition. The subject or patient is typically human, however, other suitable subjects or patients include, but are not limited to, laboratory animals, such as mouse, rat, rabbit, or guinea pig, farm animals and domestic animals or pets. Non-human primates are also included.

As used herein the terms "treating" and "treatment" refer to a reduction in severity and/or frequency of symptoms, elimination of symptoms and/or underlying cause, prevention of the occurrence of symptoms and/or their underlying cause (e.g., prophylactic therapy), improvement or remediation of damage, or reduction in intensity of infection.

As used herein, a "therapeutically effective amount" is an amount effective to elicit a cellular response that is clinically significant.

By "pharmaceutically acceptable" is meant a material that is not biologically or otherwise undesirable, i.e., the material may be incorporated into a pharmaceutical composition and administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

The methods of the present invention contemplate the administration of formulations containing thiazolide compounds. Acceptable thiazolide compounds of the invention are those disclosed in U.S. Pat. Nos. 7,645,783, 7,550,493, 7,285,567, 6,117,894, 6,020,353, 5,968,961, 5,965,590, 5,935,591, 5,886,013, which are herein incorporated by reference in their entirety. Preferred thiazolide compounds are nitazoxanide, tizoxanide or RM-4848, or its ester prodrug, RM-5038. It is understood that other prodrugs analogous or homologous to RM-5038 are also envisioned, and are an embodiment of this invention. As used herein, the term "thiazolide" refers to a thiazolide, a thiazolide analogue or a substituted thiazolide. As used herein, the term "nitazoxanide" refers to both nitazoxanide (2-(acetolyloxy)-N-(5-nitro-2-thiazolyl) benzamide) and to a nitazoxanide analogue, e.g., to one of the compounds disclosed in U.S. Pat. No. 7,285,567 or US 2007/0167504. As used herein, the term "tizoxanide" refers to tizoxanide, a tizoxanide analogue or a substituted tizoxanide. Nitazoxanide, tizoxanide, RM-4848 or any of the thiazolide analogues may be administered in the form of the compound per se, and/or, where suitable, in the form of a salt, polymorph, ester, amide, prodrug, derivative, or the like, provided the salt, polymorph, ester, amide, prodrug or derivative is suitable pharmacologically. Such salts, esters, amides, prodrugs and other derivatives of these active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). The total amount of nitazoxanide or tizoxanide in the compositions of the invention is typically about 60% to 75% by weight of the composition. The compositions may be formulated for immediate release, controlled release or sustained release. The compositions may contain one or more additional pharmaceutically acceptable additives or excipients. These excipients are therapeutically inert ingredients that are well known and appreciated in the art. As used herein, the term "inert ingredient" refers to those therapeutically inert ingredients that are well known in the art of pharmaceutical science, which can be used singly or in various combinations, and include, for example, diluents, disintegrants, binders, suspending agents, glidants, lubricants, fillers, coating agents, solubilizing agent, sweetening agents, coloring agents, flavoring agents, and antioxidants. See, for example, Remington: The Science and Practice of Pharmacy 1995, edited by E. W. Martin, Mack Publishing Company, 19th edition, Easton, Pa.

Examples of diluents or fillers include, but are not limited to, starch, lactose, xylitol, sorbitol, confectioner's sugar, compressible sugar, dextrates, dextrin, dextrose, fructose, lactitol, mannitol, sucrose, talc, microcrystalline cellulose, calcium carbonate, calcium phosphate dibasic or tribasic, dicalcium phosphaste dehydrate, calcium sulfate, and the like. The amount of diluents or fillers may be in a range between about 2% to about 15% by weight of the entire composition.

Examples of disintegrants include, but are not limited to, alginic acid, methacrylic acid DVB, cross-linked PVP, microcrystalline cellulose, sodium croscarmellose, crospovidone, polacrilin potassium, sodium starch glycolate, starch, including corn or maize starch, pregelatinized starch and the like. Disintegrant(s) typically represent about 2% to about 15% by weight of the entire composition.

Examples of binders include, but are not limited to, starches such as potato starch, wheat starch, corn starch; microcrystalline cellulose; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, and the like. The amount of binders is about 0.2% to about 14% by weight of the entire composition.

Examples of glidants include, but are not limited to, silicon dioxide, colloidal anhydrous silica, magnesium trisilicate, tribasic calcium phosphate, calcium silicate, magnesium silicate, colloidal silicon dioxide, powdered cellulose, starch, talc, and the like. The amount of glidant(s) is about 0.01% to about 0.3% by weight of the entire composition.

Examples of lubricants include, but are not limited to, magnesium stearate, aluminum stearate, calcium stearate, zinc stearate, stearic acid, polyethylene glycol, glyceryl behenate, mineral oil, sodium stearyl fumarate, talc, hydrogenated vegetable oil and the like. The amount of lubricant(s) is about 0.2% to about 1.0% by weight of the entire composition.

The compositions may contain a binder that is a low-viscosity polymer. Examples of low-viscosity polymers include, but are not limited to, low-viscosity hydroxypropyl methylcellulose polymers such as those sold by Dow Chemical under the tradename "Methocel®" (e.g., Methocel E50LV®, Methocel K100LV®, and Methocel F50LV®) and low-viscosity hydroxyethylcellulose polymers. The low-viscosity polymer is typically present at about 10% to about 20%, or about 10% to about 15%, or preferably about 12%, of the total weight of the entire composition, or, in those embodiments having controlled release and immediate release portions, the low-viscosity polymer in the controlled release portion is typically present at about 15% to about 20%, preferably about 18%, of the weight of the controlled release portion.

The compositions may further comprise a coating material. The coating material is typically present as an outer layer on the dosage form that completely covers the formulation. For example, in some embodiments, the dosage form is an oral tablet in which the controlled release portion forms a first layer of the tablet and the immediate release portion forms a second layer that is deposited on top of the first layer to form a core tablet. In such embodiments, e.g., the coating material can be in the form of an outer coating layer that is deposited on top of the core tablet. The coating material typically is about 1% to about 5% by weight of the composition, and may comprise hydroxypropylmethylcellulose and/or polyethylene glycol, and one or more excipients selected from the group comprising coating agents, opacifiers, taste-masking agents, fillers, polishing agents, coloring agents, antitacking agents and the like. Examples of film-coating substances and methods for using such coating substances are well known to those of skill in the art.

The present compositions can be used effectively to stimulate the immune system in a subject in need thereof, thereby treating or preventing a viral infection, a cancer or diseases caused by intracellular protozoan or bacterial infections. The viral infection may be influenza, in particular an influenza caused by a virus selected from H1N1, H2N2, H3N2, H5N1, H7N7, H1N2, H9N2, H7N2, H7N3, and H10N7, or Hepatitis B, or diarrhea or gastroenteritis caused by rotavirus or norovirus. The cancer may be leukemia, including hairy cell leukemia and chronic myeloid leukemia, melanoma, non-Hodgkin lymphoma, or renal cell carcinoma. The disease caused by intracellular protozoan infection may be *Cryptosporidium* spp., *Leishmania* spp., *Toxoplasma gondii*, *Trypanosoma cruzi*. The disease caused by intracellular bacterial infection may be *Mycobacterium tuberculosis*. The compositions may be administered for any length of time suitable for effectively treat or prevent a viral infection, a cancer or disease caused by intracellular protozoan infection. Any appropriate dosage and regimen may be used for the compositions. Administration can typically be carried out over a period of about 3 days to about 104 weeks, but may be carried out over a period longer than 104 weeks and may even be carried out indefinitely. Appropriate regimens can be determined by a physician.

The thiazolide compounds may be administered alone or in combination with one or more additional active agents, including a neuraminidase inhibitor, such as Laninamivir, Oseltamivir, Zanamivir or Peramivir, an immunostimulant, such as Imiquimod or Resiquimod, an adamantine analogue, and a recombinant sialidase fusion protein. The thiazolide compounds also may be administered alone or in combination with one or more additional active agents, including an antiprotozoal drug. The antiprotozoal drug may include, but is not limited to, trimethoprim/sulfamethoxazole, atovaquone, clindamycin, pyrimethamine, spiramycin, diminazine, homidium, suramin, melarsamine, sodium stibogluconate and meglumine antimoniate. The thiazolide compounds may be administered prophylactically in combination with a vaccine, or in combination with an anticancer drug. The anticancer drug may include, but is not limited to, STI571, CGP 74588, 1-β-D-Arabinofuranosylcytosine (Ara-C), doxorbicin, dacarbazine, cisplatin, bleomycin, vincristine, lomustine, vinblastine, carmustine, DTIC, tamoxifen, sunitinib, sorafenib and interferon-α. The composition and the additional active agent (e.g., an interferon) may be administered simultaneously, or separately, at the same time, or in different compositions (including in separate compositions that vary in dosage form, release profiles, and the like). It is to be understood that the description above as well as the examples that follow are intended to illustrate and not limit the scope of the invention. Other aspects, advantages and modifications within the scope of the invention will be apparent to those skilled in the art to which the invention pertains.

In subjects with immune deficiencies, the immune response required to effectively treat or prevent a viral disease, cancer or intracellular protozoan or bacterial infection may not be produced by thiazolides using the dosing regimen that is typically used to successfully treat a subject with a fully competent immune system. Subjects with extreme immune deficiencies may not be good candidates for treatment with thiazolides. Subjects with moderate immune deficiencies may require higher doses of thiazolide treatment, more frequent dosing, or dosing for a longer period of time than subjects with fully competent immune systems. Subjects with HIV infection who have not developed immune deficiencies may be effectively treated with thiazolides, while subjects with immune deficiencies associated with HIV infection may require treatment with anti-retroviral drugs to reduce HIV viral titer and partially restore immune function before or simultaneously with thiazolide therapy. Thus, the use of thiazolides to stimulate immune response may be tailored for patients based on immune status.

EXAMPLES

Example 1: Cell Preparation

Mononuclear blood cells have an important role in the immune response system, as they produce different cytokines in response to pathogen infections. Accordingly, the immunomodulatory effects of tizoxanide (TIZ) in peripheral mononuclear blood cells (PMBCs) obtained from ten (10) healthy donors and isolated by centrifugation on Ficoll-Paque. The PMBCs were cultured in RPMI-1640 media supplemented with 10% human serum in the presence or absence of three different doses of TIZ (0.5, 1.0 and 10 mg/ml) in both unstimulated and flu-stimulated conditions.

Example 2: Immunological Analyses

The unstimulated and stimulated PMBCs were analyzed for T helper and CTL activity as well as for TLR7 and TLR8 expression and type I IFN responses in the absence or presence of different doses of tizoxanide. The immunological analyses were as follows:

T helper functions were detected by determining the amount of IFNγ- and IL-2-secreting CD4+ T cells. CTL activity was detected by determining the amount of perforin-, granzyme- and Fas-expressing CD8+ T cells.

TLR expression was detected by measuring TLR8-, TLR7- and TLR3-expressing CD14+ monocytes. Tizoxanide modulation of the TLR pathway was detected by PCR array analysis of Human Type I Interferon (IFN).

Specifically, TIZ immunomodulating effects were determined in unstimulated and flu-stimulated PMBCs by analysis of the following:

Human Type I Interferon (IFN) and TLR Pathway (PCR Array):
Interferons: Ligands for Interferon-alpha and Interferon-beta Receptors: IFNA1, IFNA4, IFNB1, IFNK, IFNW1. Ligands for Interferon-gamma Receptors: IFNG. Ligands for Hematopoietin and Interferon-class (D200-domain) Cytokine Receptors: IFNA14, IFNA2, IFNA21, IFNA5, IFNA6, IFNA8, IFNE1, IL15. Other Genes Related to Interferons: IFRD1, IFRD2,
IL28A, IL29, IL6.
Interferon Receptors: Interferon-alpha and Interferon-beta Receptors: IFNAR1, IFNAR2. Interferon-gamma Receptors: IFNGR1, IFNGR2. Other Hematopoietin and Interferon-class (D200-domain) Cytokine Receptors: CNTFR, CRLF2, CSF2RA, CSF3R, EBI3, F3, IL20RB (FNDC6), IL10RA, IL10RB, IL11RA, IL12B, IL13RA1, IL20RA, IL21R, IL22RA2, IL28RA, IL2RB, IL2RG, IL31RA, IL3RA, IL4R, IL5RA, IL6R, IL7R, IL9R, LEPR, MPL, TTN.
Interferon Regulatory Factors: Transcriptional Regulators: IRF1, IRF2, IRF3, IRF4, IRF5, IRF6, IRF7, IRF8. Other Interferon Regulatory Proteins: IRF2BP1, IRF2BP2. Interferon-Inducible Proteins: Genes Involved in the Response to Virus: ISG15 (G1P2), IFI16, IFI35, IFI44, IFIH1, MX1, OAS1. Transcriptional Regulators: IFI16, SP110. Other Interferon-Inducible Genes: ADAR, CXCL10, IFI6 (G1P3), IFI27, IFI30, IFI44L, IFIT1, IFIT1L, IFIT2, IFIT3, IFITM1, IFITM2, IRGM, PSME1, PYHIN1.

Toll-Like Receptors: LY64, SIGIRR, TLR1, TLR2, TLR3, TLR4, TLR5, TLR6, TLR7, TLR8, TLR9, TLR10.

Adaptors & TLR Interacting Proteins: BTK, CD14, HMGB1, HRAS, HSPA1A, HSPD1, LY86 (MD-1), LY96 (MD-2), MAPK8IP3, MYD88, PELI1, RIPK2, SARM1, TICAM2, TIRAP, TOLLIP, TRIF.

Effectors: CASP8, EIF2AK2, FADD, IRAK1, IRAK2, MAP3K7 (TAK1), MAP3K7IP1 (TAB1), NR2C2, PPARA, PRKRA, SITPEC, TRAF6, UBE2N, UBE2V1.

Downstream Pathways and Target Genes: NFκB Pathway: CCL2, CHUK, CSF2 (GMCSF), CSF3 (GCSF), IFNA1, IFNB1, IFNG, IKBKB, IL1A, IL1B, IL2, IL6, IL8, IL10, IL12A, LTA, MAP3K1, MAP4K4, NFKB1, NFKB2, NFKBIA, NFKBIL1, NFRKB, REL, RELA, TNF, TNFRSF1A.

JNK/p38 Pathway: ELK1, FOS (c-Fos), JUN, MAP2K3, MAP2K4 (JNKK1), MAP3K1 (MEKK), MAPK8 (JNK1).

NF/IL6 Pathway: CLECSF9, PTGS2.

IRF Pathway: CXCL10, IFNA1, IFNB1, IFNG, IRF1, IRF3, TBK1.

Regulation of Adaptive Immunity: CD80, CD86, RIPK2, TRAF6.

Example 3: The Immunomodulatory Effects of Tizoxanide

Figure 3A:
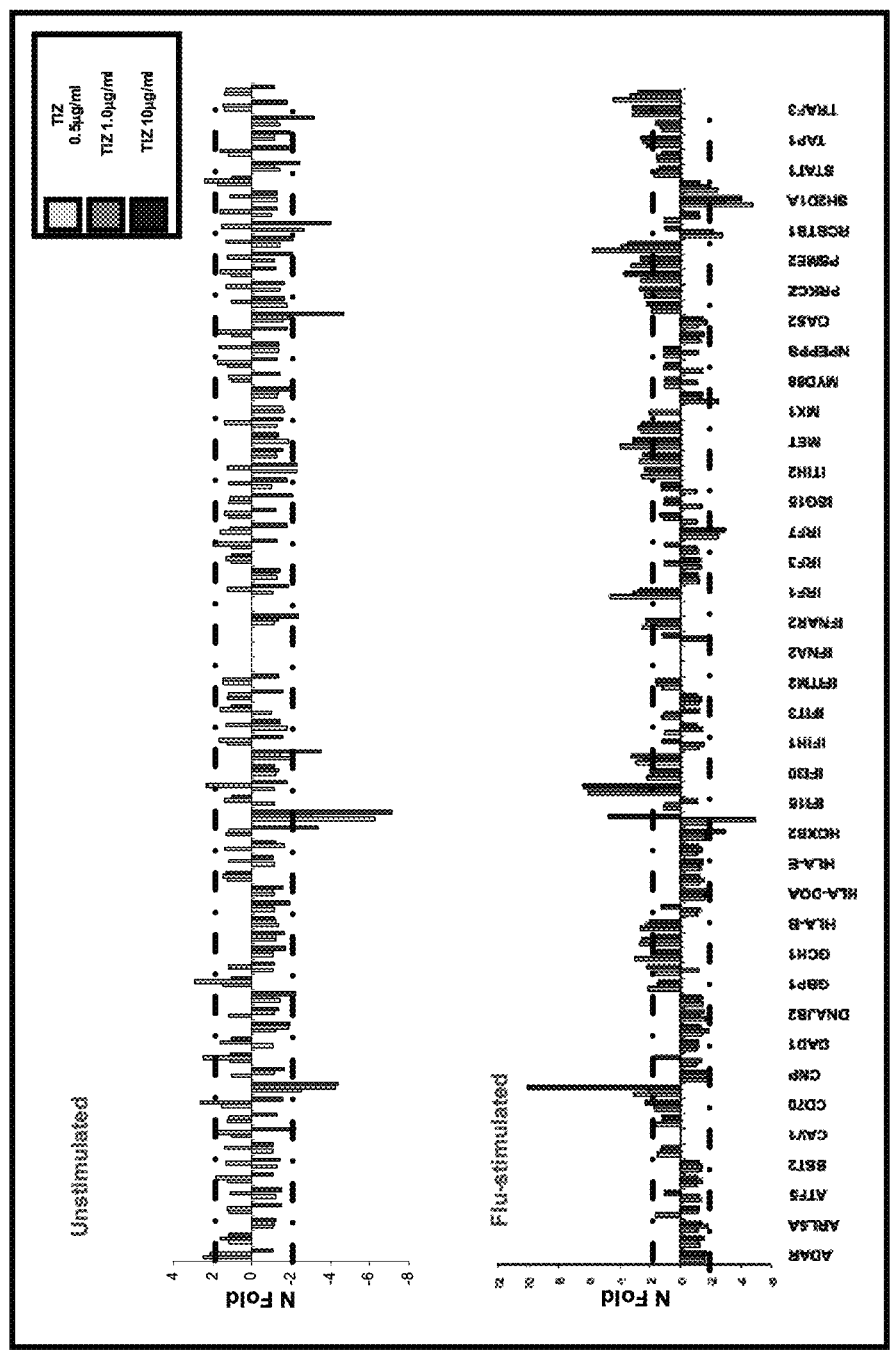
FIGS. 3A, 3B, and 3C are graphs expressing Tizoxanide modulation of the IFN pathway in unstimulated and Flu-stimulated PBMCs in the absence or presence of different doses of Tizoxanide in unstimulated and Flu-stimulated conditions. Mean values are indicated.
Figure 3B:
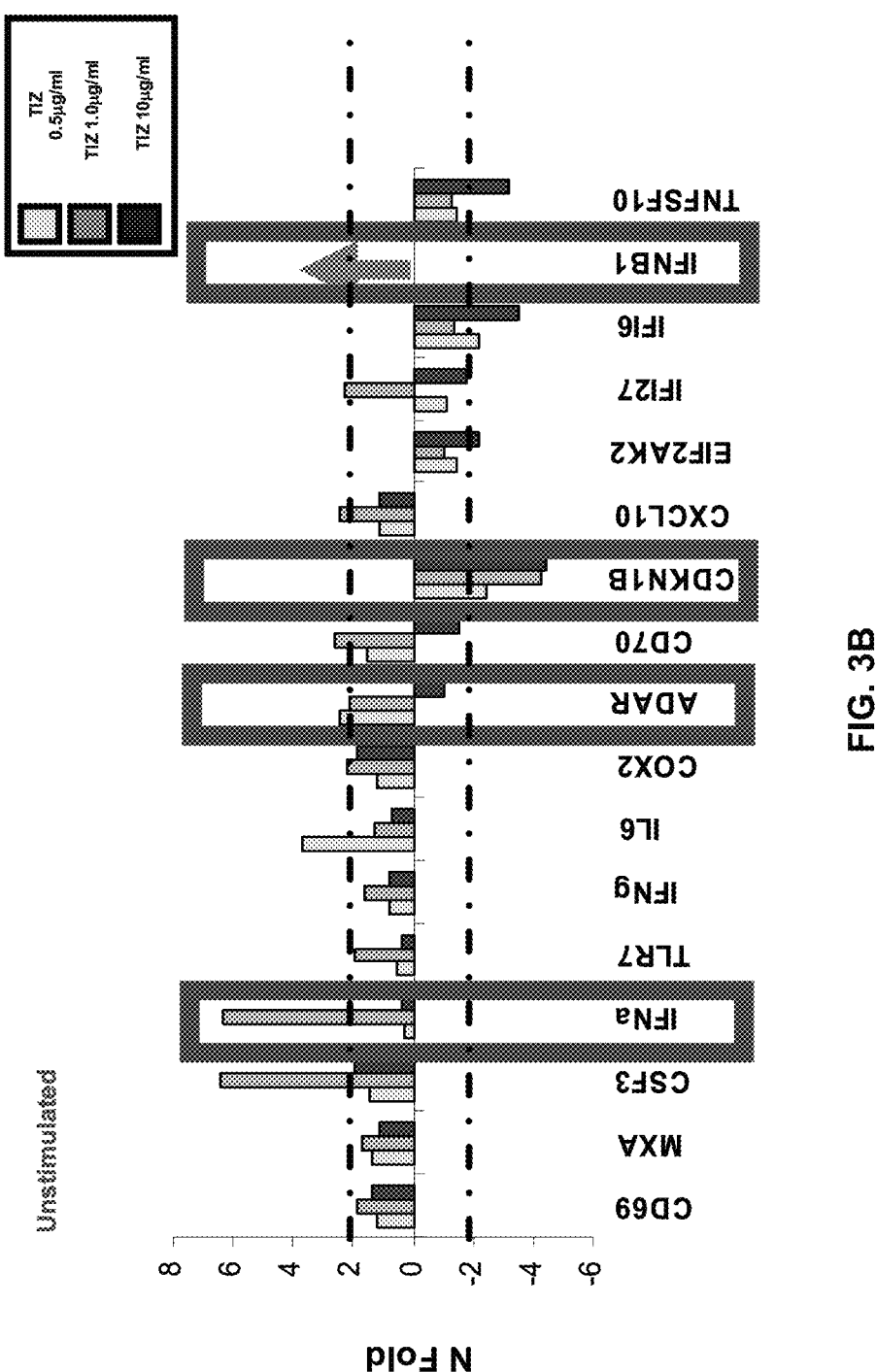
Figure 3C:
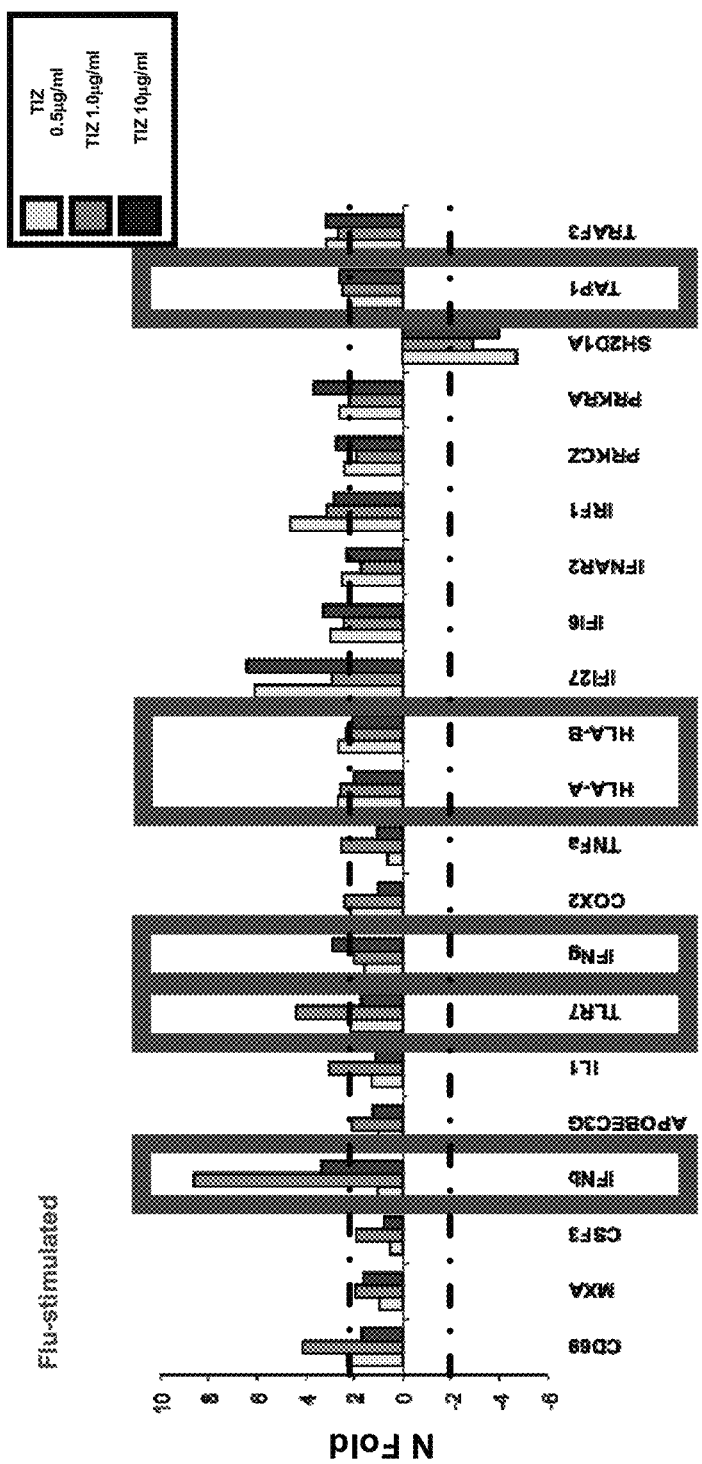

TIZ showed potent immunomodulatory effects inducing an increase in: 1) IFNγ- and IL2-secreting CD4+ T cells (FIGS. 4A and 4B); 2) CTL degranulation (FIG. 5B); 3) Fas-expressing CD8+ T cells (FIG. 5C); 4) TLR3-, TLR8- and TLR7- expression on monocytes (FIGS. 1A-C); 5) IFNα- and IFNβ-mRNA expression (FIG. 3A), 6) mRNA specific for type I IFN inducible genes (MXA, PRKCZ, ADAR, CXCL10, IRF1, PRKRA) (FIG. 3B); and 7) mRNA specific for gene involved in MHC class I presentation (HLA-A, HLA-B, TAP1) (FIG. 3C).

These results clearly demonstrate that TIZ has remarkable immunomodulatory activity and stimulates a strong immune response, which is mediated by both the innate and the acquired immune systems.

Example 4: TLR Expression on Monocytes

Figure 1B:
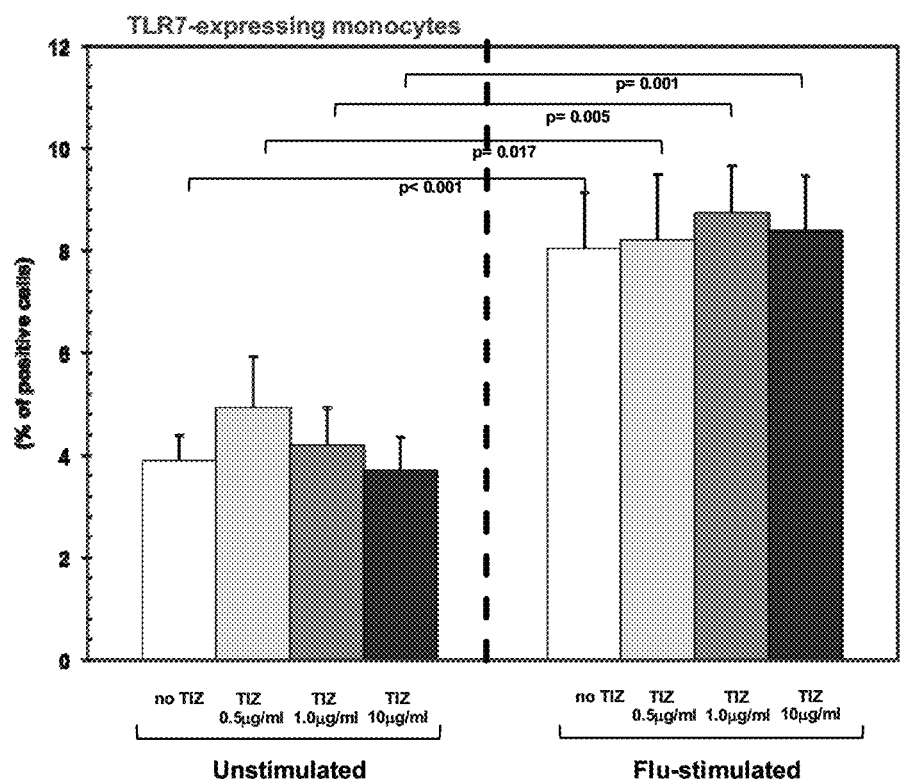
Figure 1C:
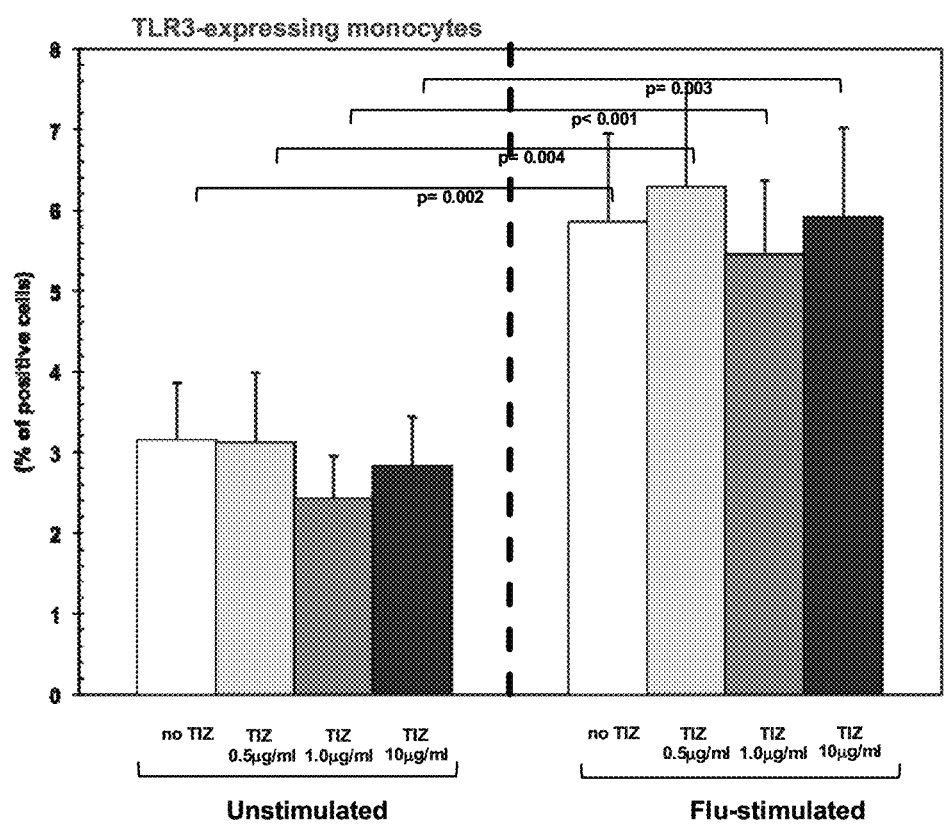

TLR3, TLR7 and TLR8 expression was evaluated on CD14+ cells (monocytes) both in un-stimulated and in flu-stimulated conditions. RM-4848 induced an increase in the percentage of in TLR7-expressing CD14+ cells compared to control upon flu-antigenic stimulation (1.0 μg/ml dose: p=0.001; 10 μg/ml dose: p=0.023), while no significative differences were observed in unstimulation condition. There was no effect on TLR3- and TLR8-expressing CD14+ cells for all five doses tested both in unstimulated and flu-stimulated conditions. (FIGS. 1A, 1B & 1C).

Example 5: TLR Pathway and RM-4848

Figure 2A:
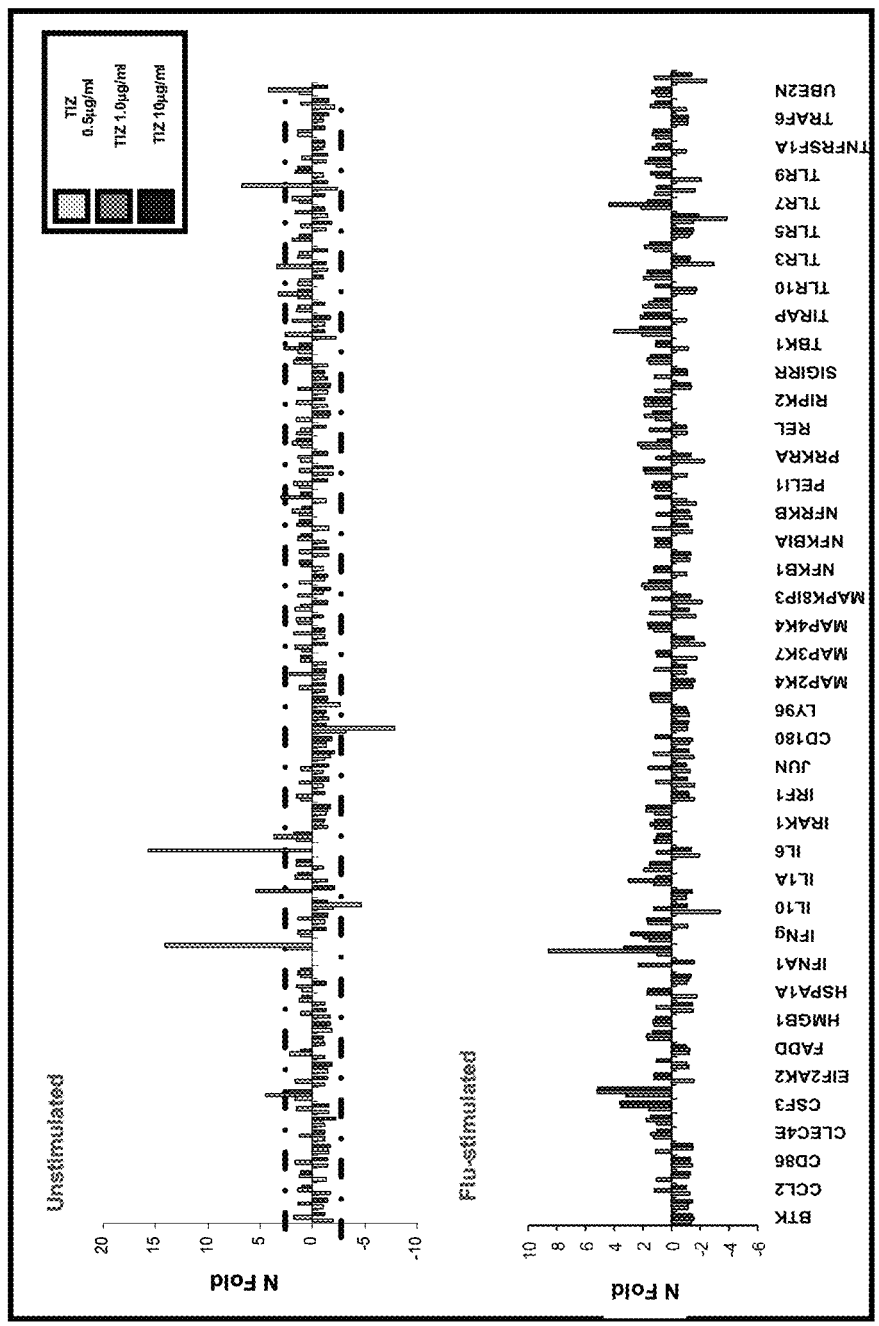
FIGS. 2A, 2B, and 2C are graphs expressing Tizoxanide modulation of the TLR pathway in unstimulated and Flu-stimulated PBMCs in the absence or presence of different doses of Tizoxanide in unstimulated and Flu-stimulated conditions. Mean values are indicated.

To determine whether an effect exerted by RM-4848 on TLR expression is dependent on a differential modulation of the TLR-associated transduction pathways, we used a Real-time PCR array, which screens for the expression of 84 genes that are involved in TLR- pathway activation. The data obtained in un-stimulated PBMC following 3 hours of incubation with RM-4848 shows that only 3 of the 84 genes are up regulated with approximately a 5-fold increase of IL1A and IL1B and a 6-fold increase of the IL6 at the 20 μg/ml dose as indicated in FIG. 2A.

Figure 2B:
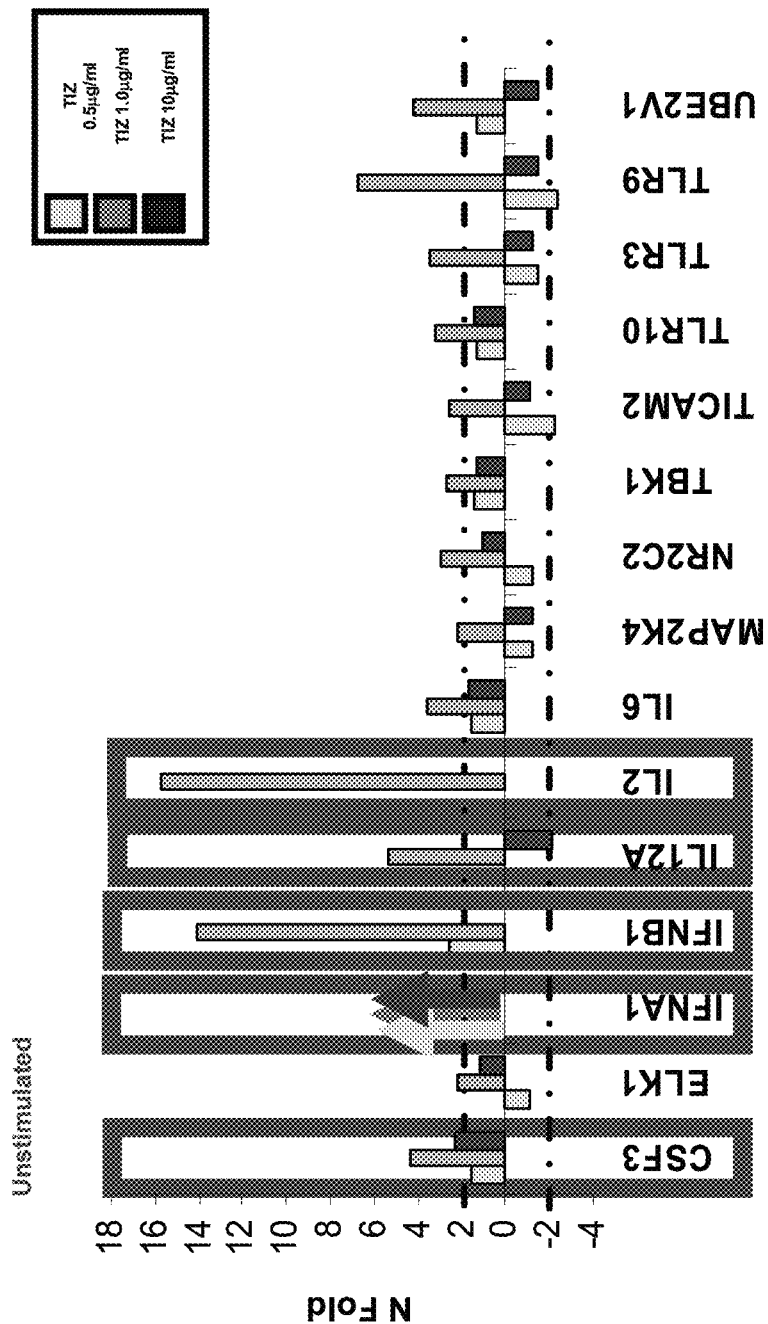
Figure 2C:
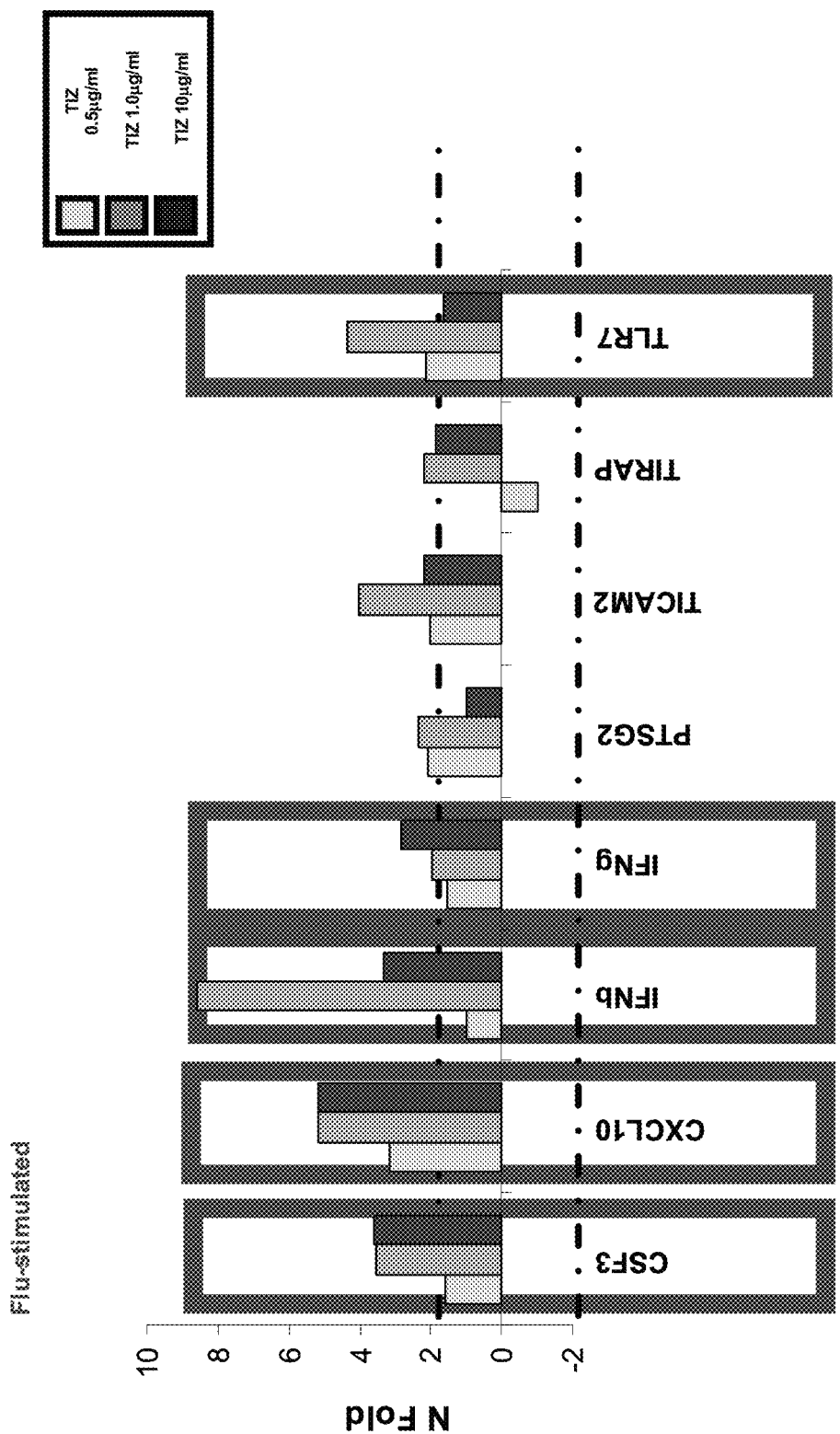

The data obtained in flu-stimulated PBMC following 3 hours of incubation with RM-4848 show that only 7 of the 84 genes were upregulated as shown in FIG. 2B. At the 1 μg/ml dose, there was approximately a 6-fold increase of INFA1 and INFB1 and a 7-fold increase in TLR3 and TLR5, a 6-fold increase for TLR9 but at the 20 μg/ml dose while TLR-7 and TLR8 were slightly above the 2-fold baseline for all doses tested.

Example 6: IFN Pathways and RM-4848

To determine whether the increases in Type I interferon expression levels in PBMC incubated with RM-4848 could influence the expression of interferon inducible genes we used a Real-time PCR array which screens for the expression of 84 genes that are involved in interferon alpha and beta response.

Results of the analyses performed in un-stimulated PBMC incubated with RM-4848 showed that none of the 84 genes tested were up-regulated, at the contrary 16 genes were down regulated. In particular, a 20-fold decrease for INFA1, a 15-fold decrease for INFA2 and INFB1, and a 10-fold decrease in INFA4 at the high 20 μg/ml dose were reported. This down-regulating effects were not seen at the two lower doses of 1 and 10 μg/ml (FIG. 3A).

Results of the analyses performed in flu-stimulated PBMC incubated with RM-4848 showed that 12 of the 84 genes tested were up regulated. The data obtained in flu-stimulated PBMC following 3 hours of incubation with RM-4848 show a 10-fold increase for INFA1 and INFA4, a 8-fold increase for INFB1 and a 6-fold increase for IFNA2 at the low 1 μg/ml dose. The three dose levels moderately up-regulated the ISGs, IFI27 and IFIT1 with a more pronounced effect at the 10 μg/ml dose (>4-fold) (FIG. 3B).

Example 7: T Helper Functions and RM-4848

Figure 4A:
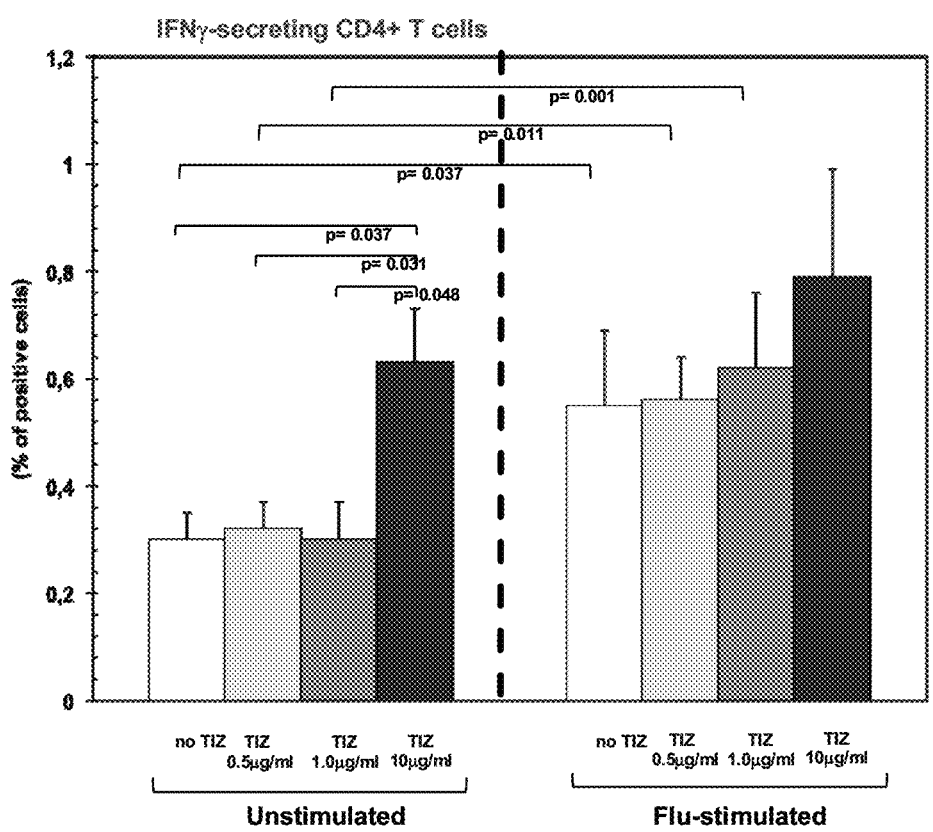
FIGS. 4A and 4B are graphs expressing T helper functions IFNg- and IL2-secreting CD4+ T cells in the absence or presence of different doses of Tizoxanide in unstimulated and Flu-stimulated conditions. Mean values, S.E. and p values are indicated.
Figure 4B:
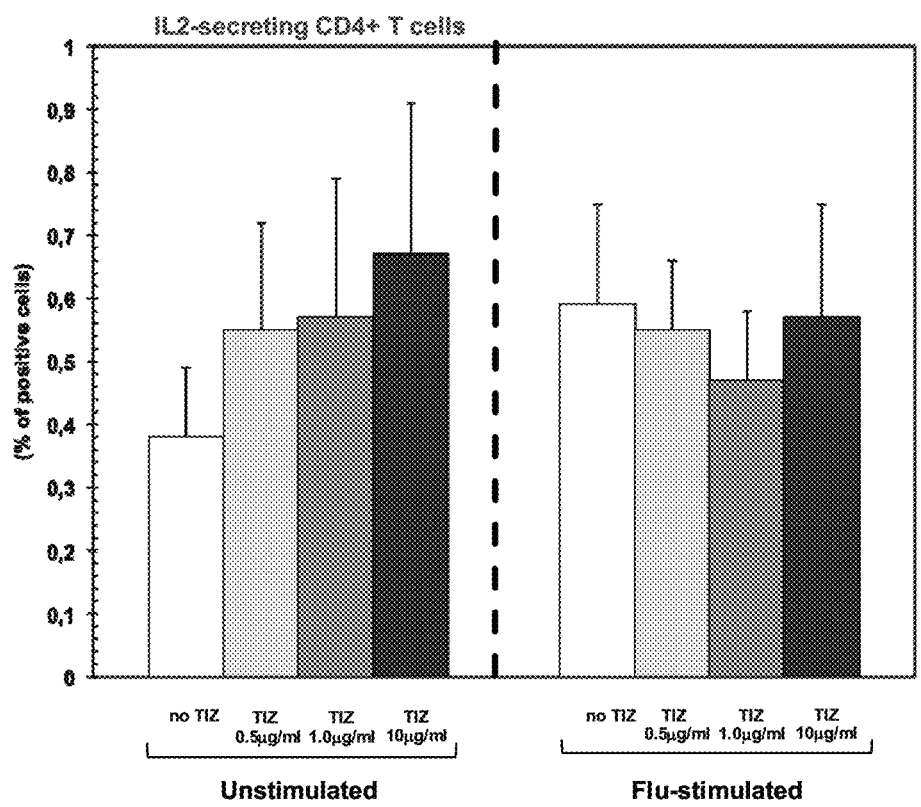

IFN-γ and IL2 production by CD4+ T cells was evaluated both in basal condition and after stimulation with Flu-specific antigens. The low 0.5 μg/ml dose of RM-4848 induced a statistically significant upregulation in IFN-γ production in un-stimulated cells (p=0.035) and in stimulated conditions (p=0.050) (FIG. 4A). A similar trend was observed in IL2-secreting CD4+ T cells in both un-stimulated (0.5 μg/ml dose: p=0.047) and Flu-stimulated conditions (0.5 μg/ml dose: p=0.037) (FIG. 4B).

Example 8: CTL Activity and RM-4848

Figure 5A:
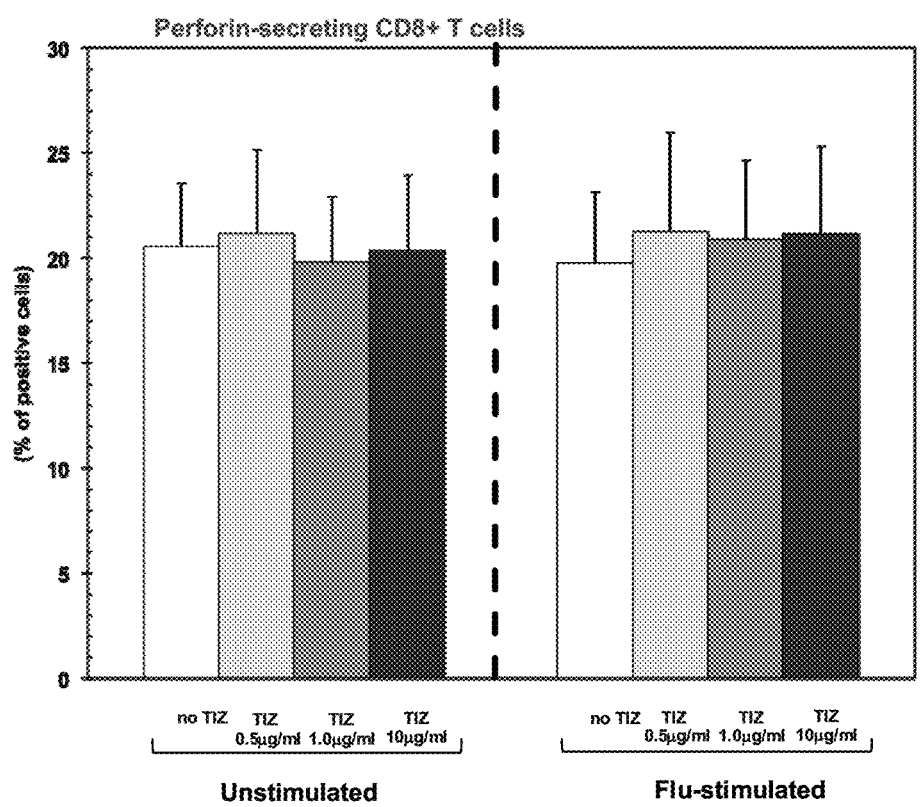
FIGS. 5A, 5B, and 5C are graphs expressing Cytotoxic T cell functions. Perforin-, granzyme-, and Fas-expressing CD8+ T cells in the absence or presence of different doses of Tizoxanide in unstimulated and Flu-stimulated conditions. Mean values, S.E. and p values are indicated.
Figure 5B:
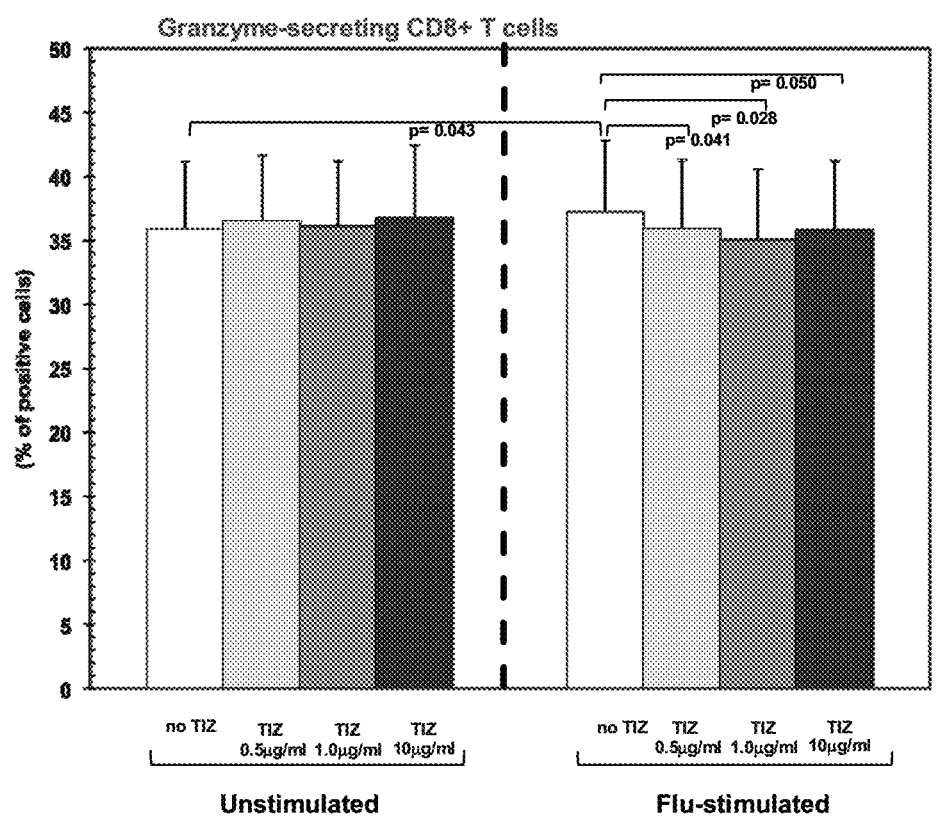
Figure 5C:
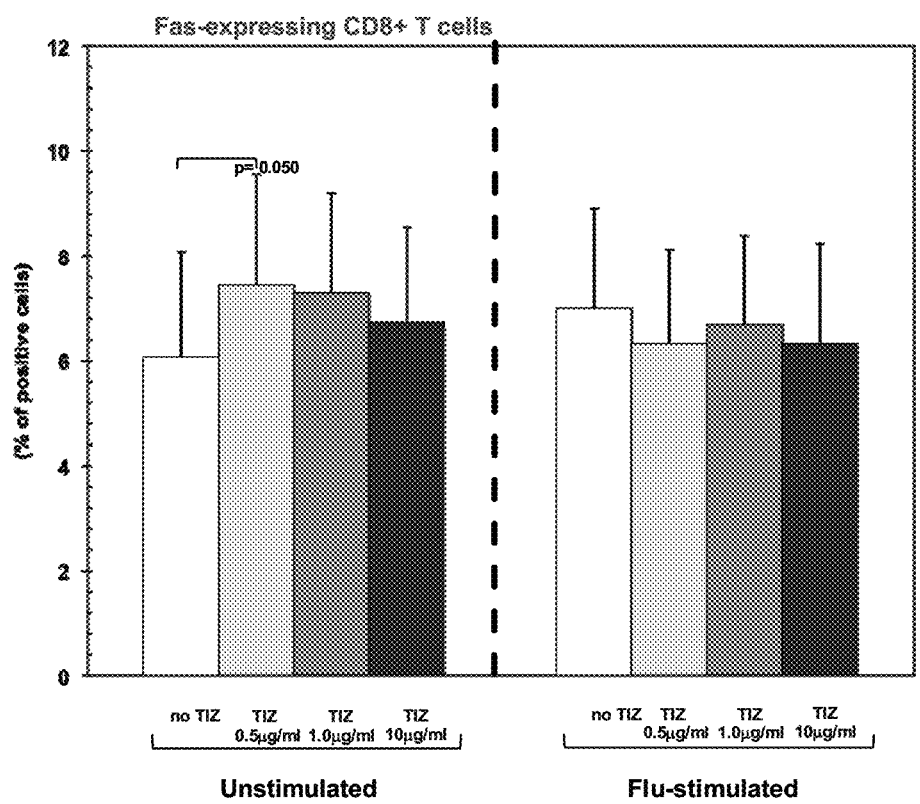
Figure 6A:
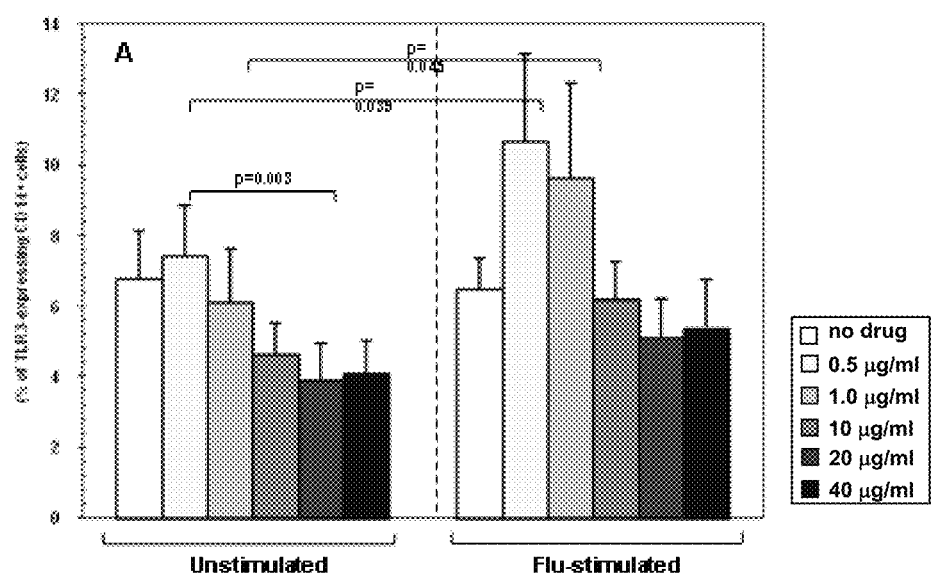
FIGS. 6A, 6B, and 6C are graphs expressing percentage of TLR3- (FIG. 6A), TLR7-(FIG. 6B) and TLR8- (FIG. 6C) expressing CD14+ cells in unstimulated and flu-stimulated conditions. Data obtained in the absence or in the presence of five different doses of RM4848 (0.5 µg/ml; 1.0 µg/ml; 10 µg/ml; 20 µg/ml; 40 µg/ml) are indicated. Mean values, S.E. and p values are shown.
Figure 6B:
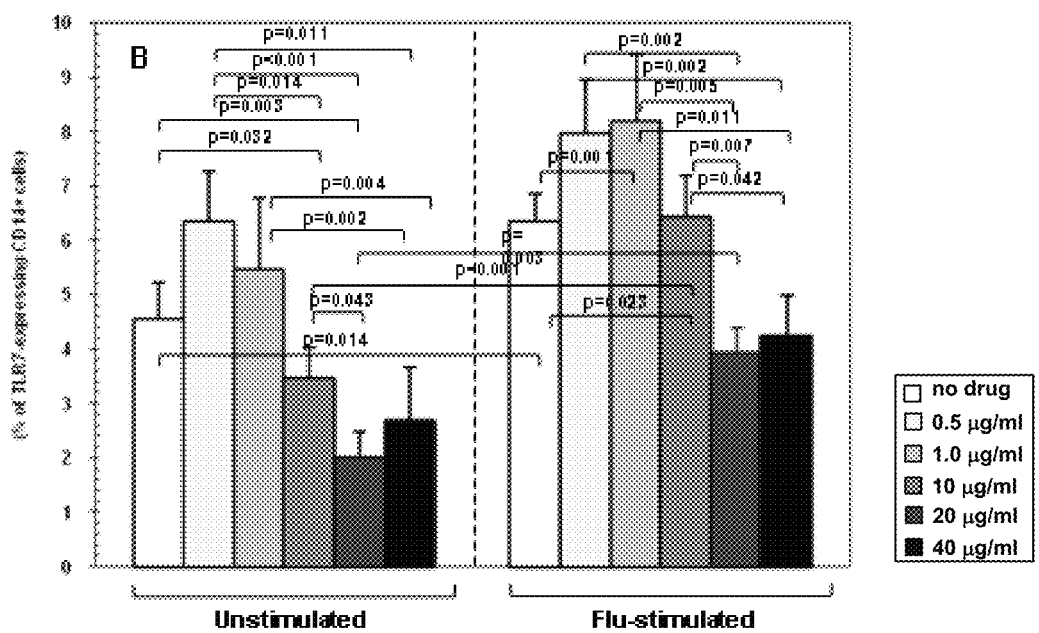
Figure 6C:
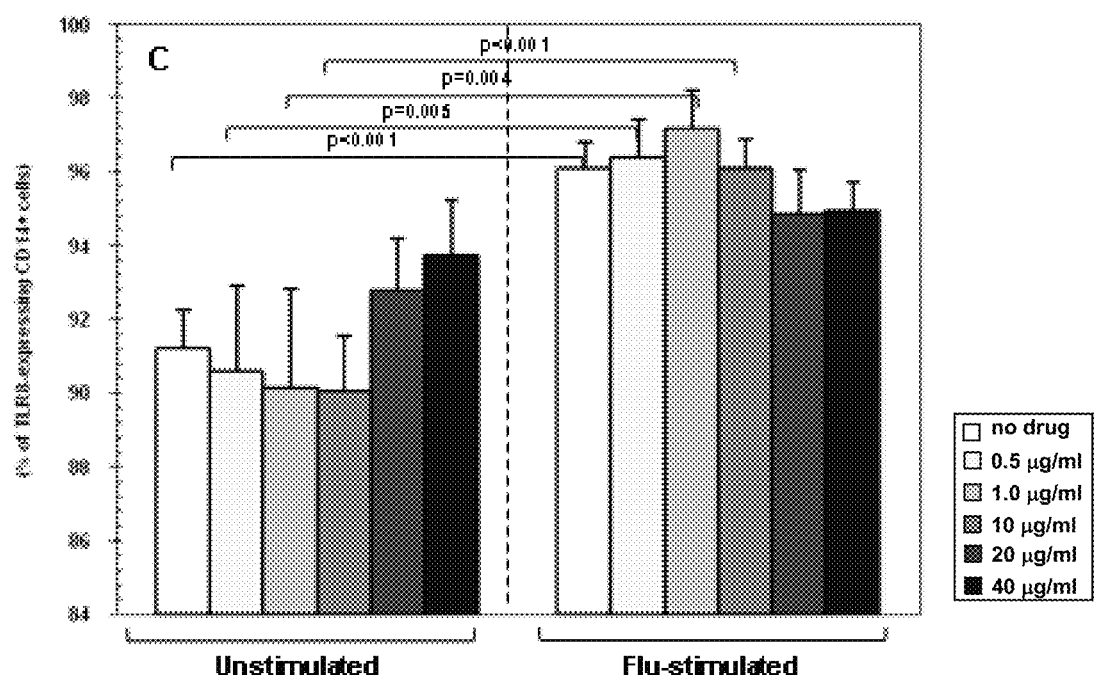
Figure 7A:
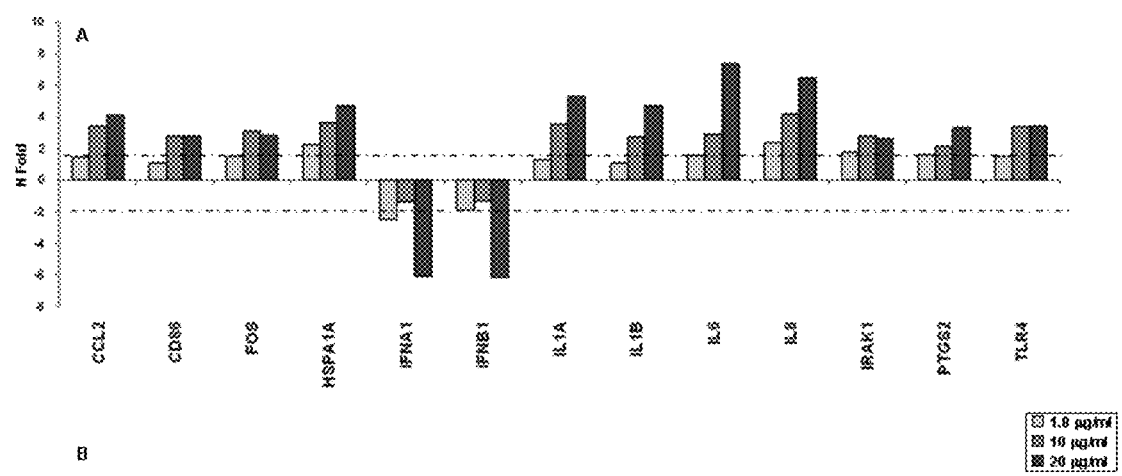
FIGS. 7A and 7B are graphs expressing toll-Like Receptor signalling pathway mRNA expression following stimulation with three different doses of RM4848 (1.0 µg/ml; 10 µg/ml; 20 µg/ml) in un-stimulated (FIG. 7A) and flu-stimulated (FIG. 7B) conditions. The expression of 84 genes involved in the Toll-Like Receptor signalling pathway has been assessed by real-time quantitative RT-PCR, calculated relative to five housekeeping genes and shown as fold-change expression from the unstimulated sample. Only the targets showing different expression levels following Tizoxanide stimulation are indicated in the figure.
Figure 7B:
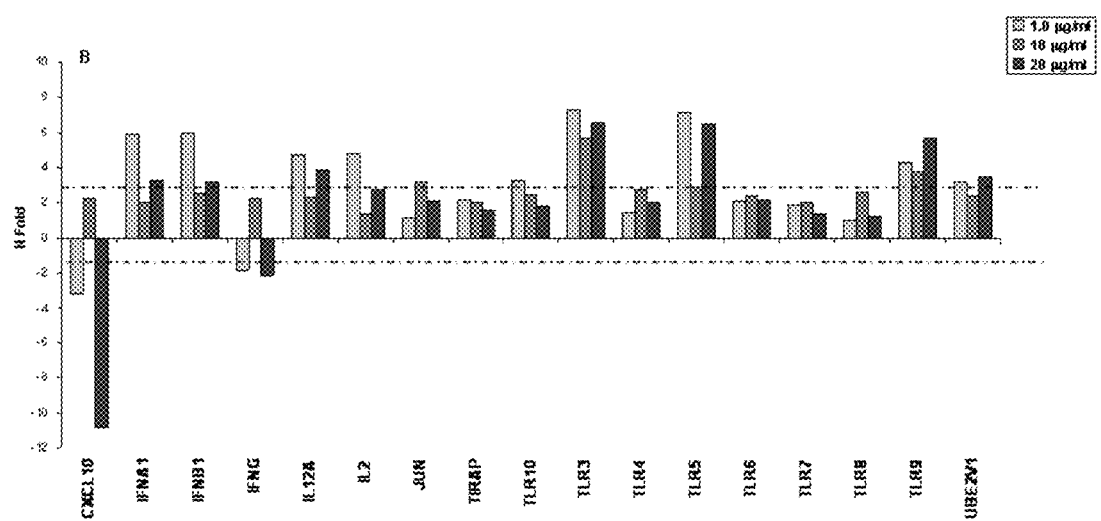
Figure 8A:
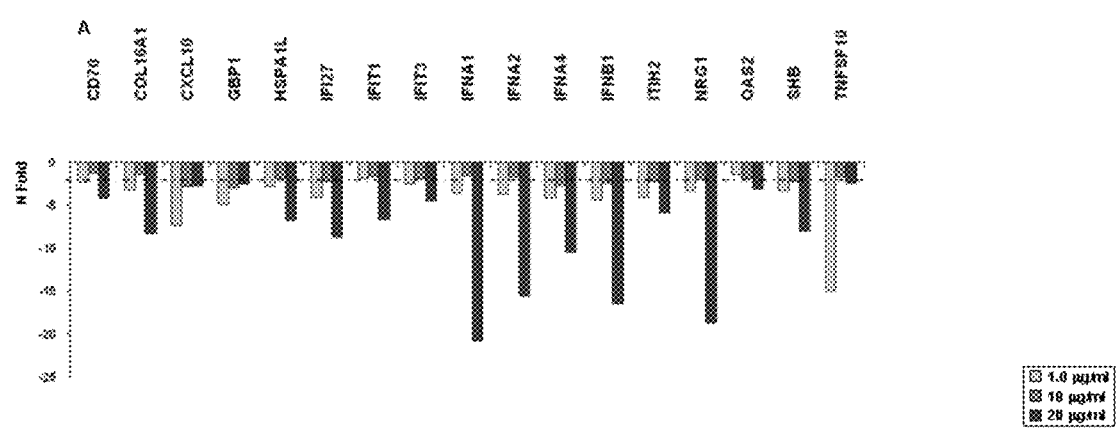
FIGS. 8A and 8B are graphs expressing type I interferon signalling pathway mRNA expression following stimulation with three different doses of RM4848 (1.0 µg/ml; 10 µg/ml; 20 µg/ml) in un-stimulated (FIG. 8A) and flu-stimulated (FIG. 8B) conditions. The expression of 84 genes involved in the Type I interferon signalling pathway has been assessed by real-time quantitative RT-PCR, calculated relative to five housekeeping genes and shown as fold-change expression from the unstimulated sample. Only the targets showing different expression levels following Tizoxanide stimulation are indicated in the figure.
Figure 8B:
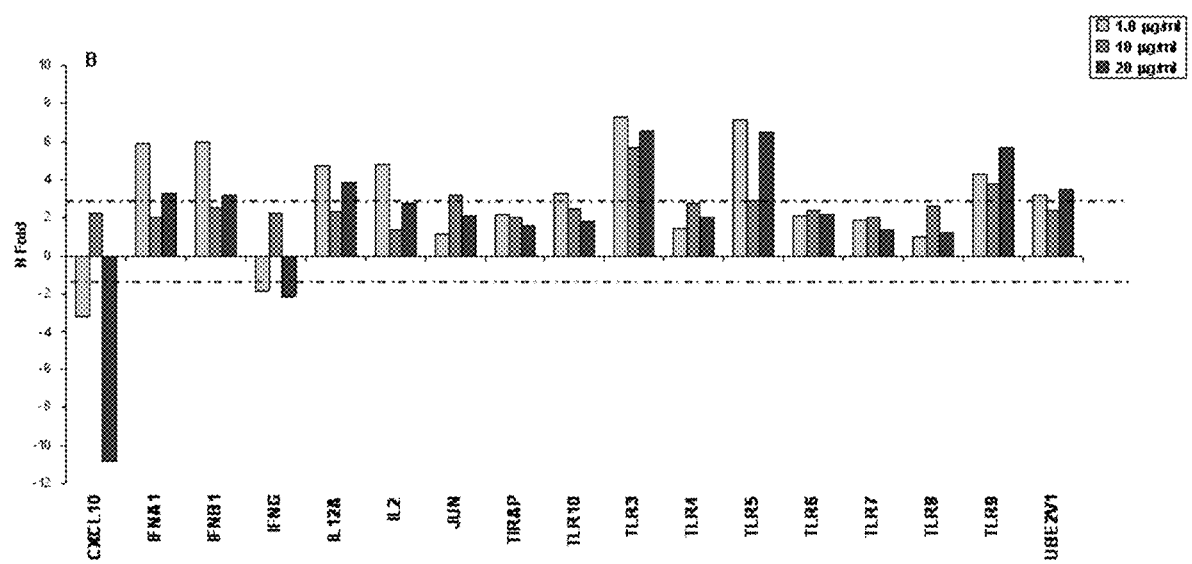
Figure 9A:
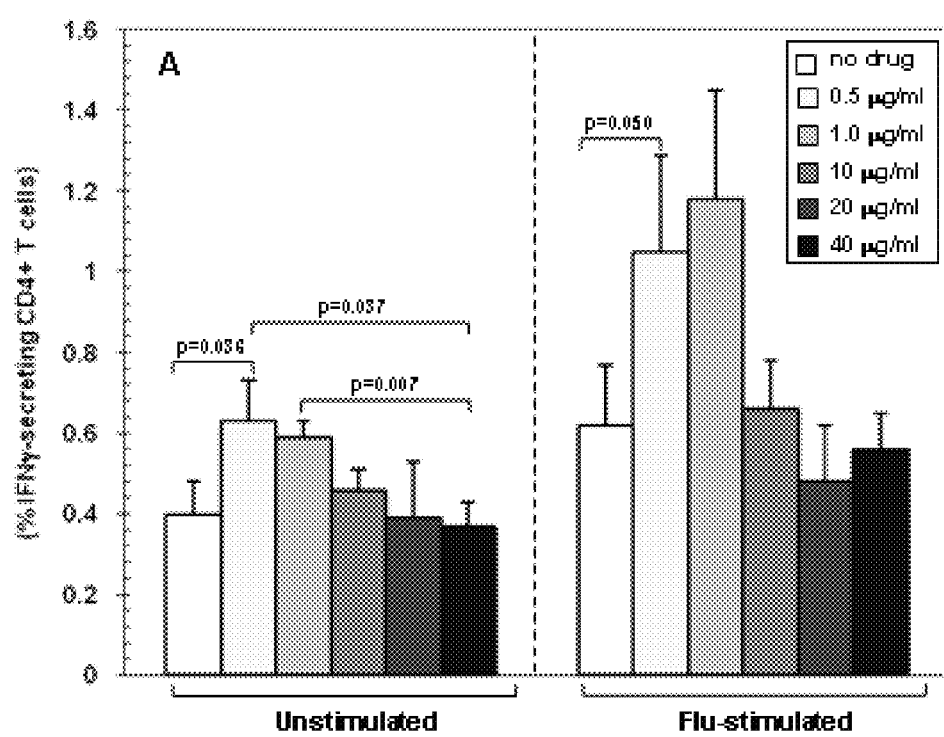
FIGS. 9A and 9B are graphs expressing percentage of IFNγ- (FIG. 9A) and IL2-(FIG. 9B) secreting CD4+ T cells in unstimulated and flu-stimulated conditions. Data obtained in the absence or in the presence of five different doses of RM4848 (0.5 µg/ml; 1.0 µg/ml; 10 µg/ml; 20 µg/ml; 40 µg/ml) are indicated. Mean values, S.E. and p values are shown.
Figure 9B:
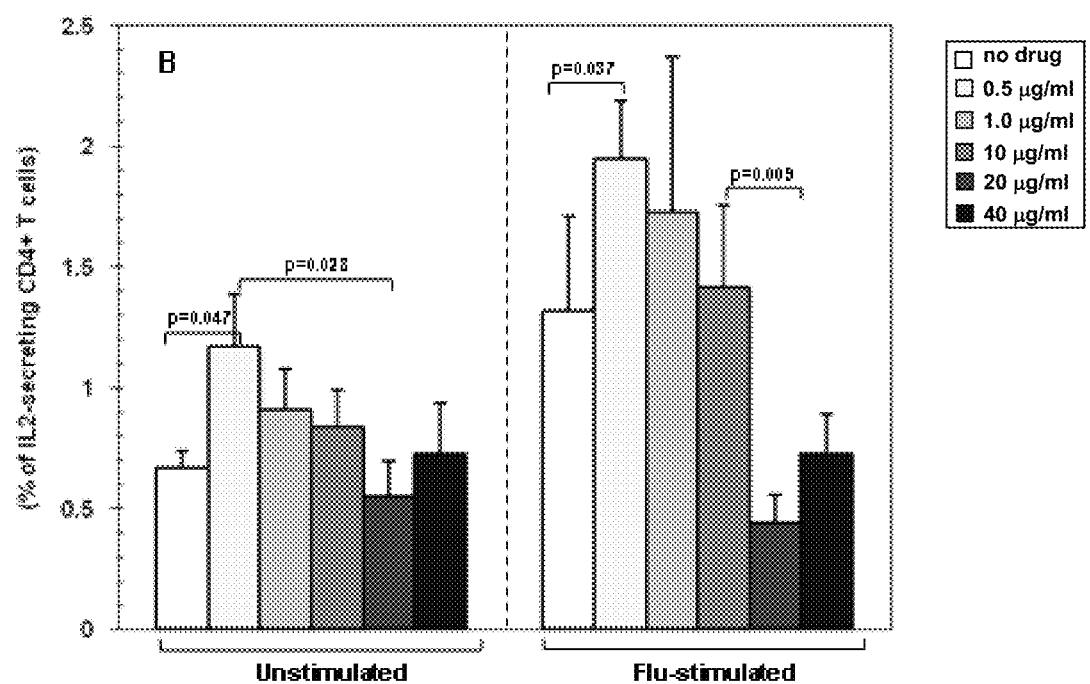
Figure 10A:
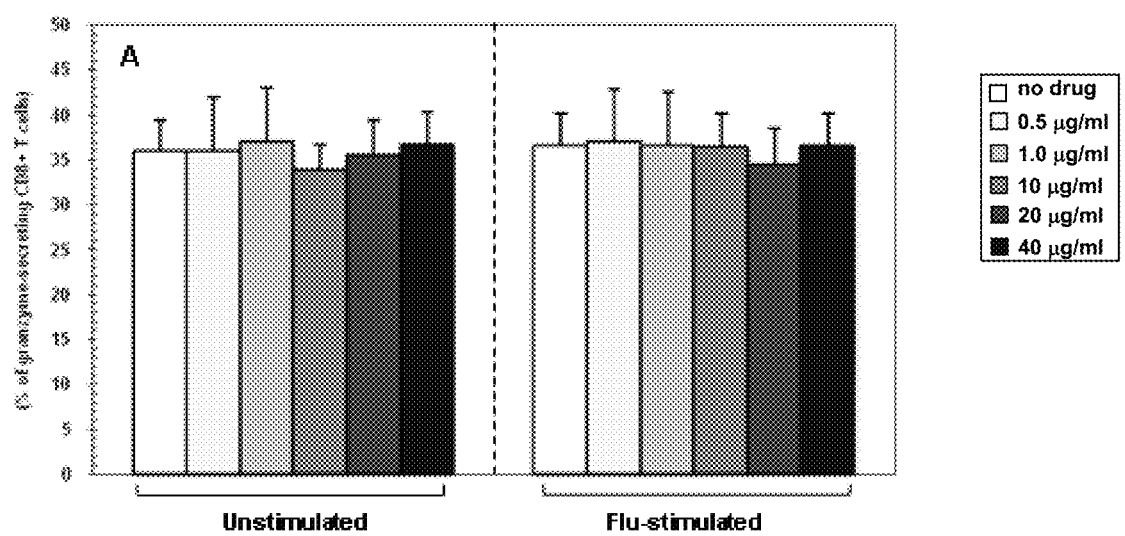
FIGS. 10A, 10B, and 10C are graphs expressing an embodiment of the invention wherein percentage of granzyme- (FIG. 10A), perforin- (FIG. 10B) and Fas- (FIG. 10C) expressing CD8+ T cells in unstimulated and flu-stimulated conditions. Data obtained in the absence or in the presence of five different doses of RM4848 (0.5 µg/ml; 1.0 µg/ml; 10 µg/ml; 20 µg/ml; 40 µg/ml) are indicated. Mean values, S.E. and p values are shown.
Figure 10B:
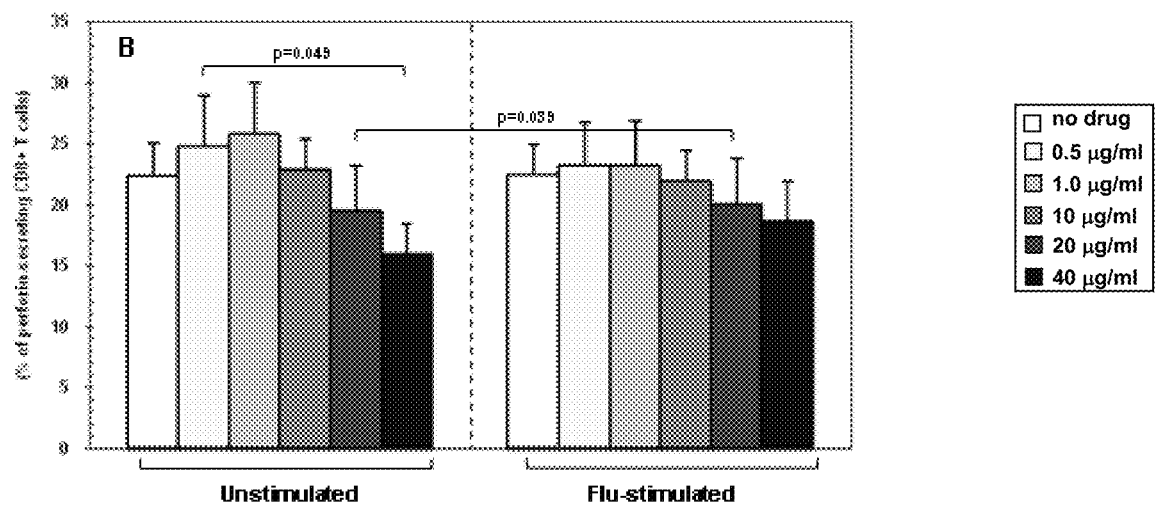
Figure 10C:
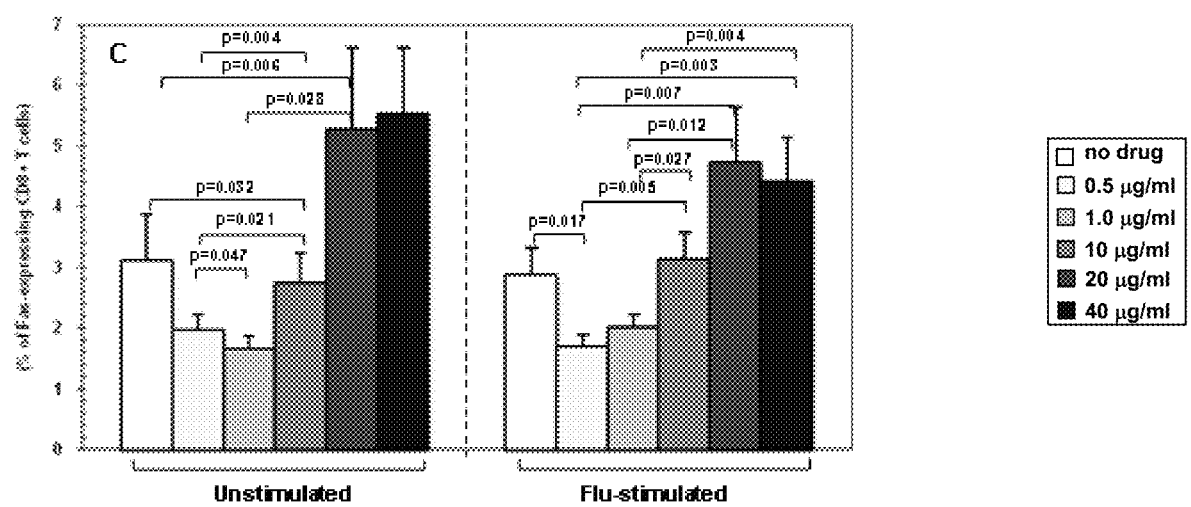
Figure 11:
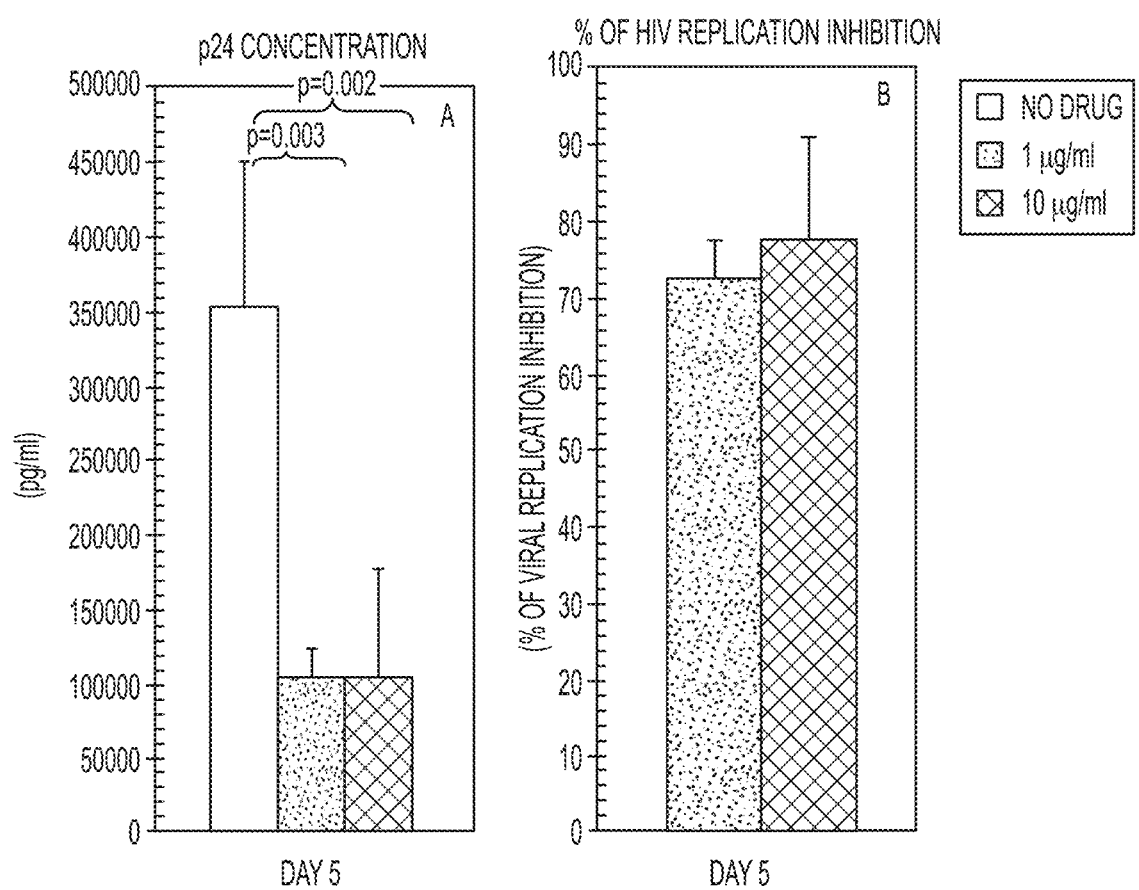
FIG. 11 shows graphs expressing an embodiment of the invention wherein inhibition of HIV-1 replication: p24 levels in PBMC exposed to HIV (Panel A) and percentage of HIV replication inhibition (Panel B) in the absence/presence of different doses of tizoxanide (1.0 µg/ml; 10 µg/ml) are evaluated at 5 days post-infection. Mean values, S.E., and p values are indicated.

Granzyme-, Perforin- and Fas-expressing CD8+ T cells were analysed in unstimulated condition and upon Flu-antigen-stimulation. RM-4848, at the three higher dose levels tested, induced a degranulation of CTLs, evaluated by reduction in perforin expression (FIG. 5B). The percentage of Fas-expressing CD8+ T cells was also statistically significantly increased in the presence of the higher 20 and 40 µg/ml RM-4848 doses both in un-stimulated (p=0.006) in stimulated conditions (p=0.003) (FIG. 5C).

From Examples 4-8 it is apparent that there is an up regulation and activation of TLR especially directly with TLR7 resulting a selective increase of type 1 interferon (IFN-α, IFN-β) production, with subsequent activation of interferon-stimulated gene pathways (IsG). More specifically Type I IFN inducible genes (CD70, COL16A1, HSPA1L, IFI27, IFIT1, NRG1 and SHB) are upregulated. These genes are all involved in controlling viral replication. RM4848 activates at the same time CD4+ and CD8+ T-lymphocytes. In particular, in CD4+ T-lymphocite there is an upregulation of INF-γ and IL-2 production, while in CD8+ T cells are induced to degranulate, consistent with an activation of cell mediated immunity.

These results support the broad-spectrum antiviral activity of RM4848, which stimulates the immune system to fight viral infection. It is particularly remarkable that the drug is not only stimulating an innate immune response probably responsible for clearing most infections before they cause perceptible disease even if many pathogens have evolved mechanisms for obstructing their detection. From a clinical standpoint it would suggest that RM4848 and likely the other thiazolides with a similar immuno-stimulating profile could be used to prevent diseases or to limitate the spread of a disease. The activity of RM4848 against the adaptive immunity is not only remarkable because it comes in addition to its effect against innate immunity but also because it is the mechanism by which viral diseases are cured. Adaptive immunity is based on lymphocytes, which have a single type of receptors but an essentially unlimited repertoire of variants recognizing antigens, an operationally defined term that reflects their versatility. In addition to the productions of several lymphocytes, helpers or killers they will culminate with the production of antibodies by the B cells. If adaptive immunity is delayed to a few days upon the onset of a specific infection, its action in producing particles toxic to the pathogen and the development of immune memory are a most powerful anti-viral mechanism that that observed with innate immunity while both are necessary and inter-related.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A method of inhibiting a replication of HIV comprising administering to a subject in need thereof a therapeutically effective amount of a thiazolide compound, wherein the thiazolide compound is nitazoxanide, tizoxanide, a mixture nitazoxanide and tizoxanide, N-(5-chlorothiazol-2-yl)-2-hydroxybenzamide, or a salt, ester, or amide thereof.

2. The method of claim 1, wherein the thiazolide compound is nitazoxanide, tizoxanide or a mixture thereof.

3. The method of claim 2, wherein the thiazolide compound is administered orally.

4. The method of claim 1, wherein the thiazolide compound is N-(5-chlorothiazol-2-yl)-2-hydroxybenzamide.

5. The method of claim 1, wherein the thiazolide compound is administered in combination with a vaccine.

6. The method of claim 1, wherein the thiazolide compound is administered in combination with an immunostimulant.

7. The method of claim 1, wherein said administering stimulates an immune response in subject.

8. The method of claim 1, wherein said administering stimulates T helper cell or CTL activity, TLR7 or TLR8 expression or type I interferon response in the subject.

9. The method of claim 8, wherein said administering induces an increase in at least one of 1) IFNγ and IL2-secreting CD4+ T cells, 2) CTL degranulation, 3) Fas-expressing CD8+ T cells, 4) TLR8-expressing monocytes, 5) IFNα, and IFNβ-mRNA expression, 6) mRNA specific for a type 1 IFN inducible gene and 7) mRNA specific for a gene involved in MHC class I presentation.

10. The method of claim 1, wherein the HIV is HIV-1.

11. The method of claim 1, wherein the subject does not have an immune deficiency.

12. The method of claim 1, wherein the subject has an immune deficiency.

13. The method of claim 12 further comprising administering an antiretroviral drug to the subject before or simultaneously with said administering the thiazolide compound.

14. The method of claim 1, wherein said administering reduces a p24 concentration in the subject.

* * * * *